United States Patent [19]

Hazato et al.

[11] Patent Number: 5,149,859
[45] Date of Patent: Sep. 22, 1992

[54] NAPHTHALENE DERIVATIVES

[75] Inventors: Atsuo Hazato; Takumi Takeyasu, both of Hino; Koji Tomimori, Hachioji; Yoshinori Kato, Hino, all of Japan

[73] Assignee: Teijin Limited, Osaka, Japan

[21] Appl. No.: 582,443

[22] Filed: Sep. 14, 1990

[30] Foreign Application Priority Data

Sep. 14, 1989 [JP] Japan ................... 1-239460
Sep. 29, 1989 [JP] Japan ................... 1-252325
Oct. 16, 1989 [JP] Japan ................... 1-266211

[51] Int. Cl.$^5$ ................ C07C 321/22; C07C 229/14; C07C 69/66; C07C 251/18
[52] U.S. Cl. ...................... 560/10; 560/39; 560/53; 562/427; 562/440; 562/462
[58] Field of Search ............ 560/39, 10, 53; 562/433, 440, 427, 462

[56] References Cited

U.S. PATENT DOCUMENTS 4,568,684  2/1986  Rentzea et al. ............ 560/43 X
4,916,157  4/1990  Moser et al. ............... 560/43 X

FOREIGN PATENT DOCUMENTS 0149588  7/1985  European Pat. Off.

OTHER PUBLICATIONS

Tateson et al., Br. J. Pharmacol., (1988), 94: pp. 528-539.
Journal of Medicinal Chemistry, vol. 31, No. 3 (1988), p. 500.
Journal of Medicinal Chemistry, vol. 31, No. 1, (1988), pp. 3-5.
Journal of Medicinal Chemistry, vol. 33, No. 3, (1990), pp. 992-998.
Journal of Medicinal Chemistry, vol. 30, No. 3, (1987), pp. 574-580.
Journal of Medicinal Chemistry, vol. 31, No. 10, (1988), pp. 1960-1964.
Journal of Medicinal Chemistry, vol. 32, No. 8, (1989), pp. 1836-1842.

Primary Examiner—Jose G. Dees
Assistant Examiner—Vera C. Clarke
Attorney, Agent, or Firm—Sughrue, Mion, Zinn, Macpeak & Seas

[57] ABSTRACT

A naphthalene derivative having the formula (I):

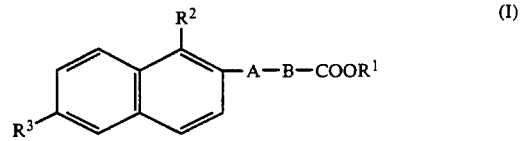

wherein $R^1$ represents a hydrogen atom, a $C_1$-$C_5$ alkyl group or a non-toxic salt moiety; $R^2$ and $R^3$ independently represent a hydrogen atom or —$OR^4$ where $R^4$ represents a hydrogen atom or a $C_1$-$C_3$ alkyl group;

A represents a group:

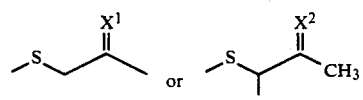

[where $X^1$ and $X^2$ represents an oxygen atom or N—$OR^5$ (where $R^5$ represents a hydrogen atom or a $C_1$-$C_3$ alkyl group)], a group:

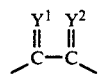

[where $Y^1$ and $Y^2$ independently an oxygen atom or a group N—$OR^6$ (where $R^6$ represents a hydrogen atom or a $C_1$-$C_3$ alkyl group)], or a group:

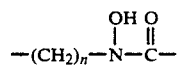

(where n is 0 or 1); and
B represents —$(CH_2)_m$—
wherein m is an integer of 1, to 8,

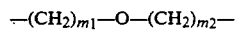

wherein $m_1$ and $m_2$ are independently 1 or 2, or

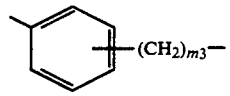

wherein $m_3$ is 0 or 1.

7 Claims, No Drawings

NAPHTHALENE DERIVATIVES

BACKGROUND OF THE INVENTION

1. Field of the Invention

The present invention relates to a naphthalene derivative useful as a pharmaceutical, and a preparation method thereof. More specifically, it relates to a naphthalene derivative having a therapeutic action against diseases caused by arachidonic acid cascade methabolites, and a method of preparing the same. 2. Description of the Related Art Arachidonic acid in the living body is converted through the action of lipoxygenase into various leukotrienes (LT), and these leukotriens have various physiological activities. For example, $LTB_4$ precipitates in the chemotactic activity of leucocyte, infiltration, aggregation, degranulation, superoxide anion production, adherence sthenia into, for example, blood vessel endothelium, and $LTC_4$ and $LTD_4$ exhibit a smooth muscle contraction of the ileum, respiratory organ system, skin blood vessel contraction, blood vessel permeability sthenia, hypotension. (The Leukotrienes, A Biological Council Symposium, P. J. Piper, Raven Press (New York)).

Currently, leukotrienes exhibiting these various physiological activities are known to cause allergic diseases such as bronchial asthma, nasal allergy, opthalmia, atopic dermatitis, edema, ischemic diseases, and circulatory system diseases such as hypertension and ischemic cerebral disorder, etc. Further, it has been clarified by recent studies that a large amount of $LTB_4$ is observed in lesions of psoriasis.

Accordingly, an inhibition of lipoxygenase is considered to be an effective therapy of, for example, allergic diseases, circulatory system diseases or psoriasis, and inflammations associated therewith.

SUMMARY OF THE INVENTION

Accordingly, the objects of the present invention are to eliminate the above-mentioned disadvantages of the prior art and to provide a substance inhibiting biosynthesis of the chemical mediator such as leukotrienes produced by lipoxygenase.

Other objects and advantages of the present invention will be apparent from the following description.

In accordance with the present invention, there is provided a naphthalene derivative having the formula (I):

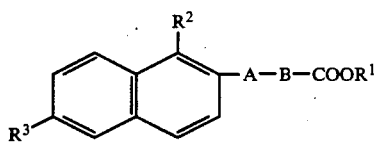

wherein $R^1$ represents a hydrogen atom, a $C_1$-$C_5$ alkyl group or a non-toxic salt moiety;

$R^2$ and $R^3$ independently represent a hydrogen atom or $-OR^4$ where $R^4$ represents a hydrogen atom or a $C_1$-$C_3$ alkyl group;

A represents a group:

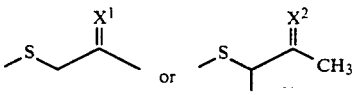

[where $X^1$ and $X^2$ represents an oxygen atom or N—$OR^5$ (where $R^5$ represents a hydrogen atom or a methyl group)], a group:

[where $Y^1$ and $Y^2$ independently represent an oxygen atom or a group N—$OR^6$ (where $R^6$ represents a hydrogen atom or a methyl group)], or a group:

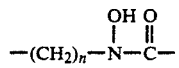

(where n is 0 or 1); and
B represents —$(CH_2)_m$—
wherein m is an integer of 1 to 8,

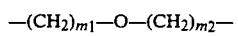

where $m_1$ and $m_2$ are independently 1 or 2, or

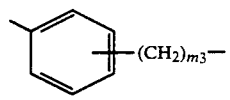

wherein $m_3$ is 0 or 1.

DESCRIPTION OF THE PREFERRED EMBODIMENTS

The novel naphthalene derivatives according to the present invention having the above formula (I) will now be explained hereinbelow.

In the formula (I), $R^1$ represents a hydrogen atom, a $C_1$-$C_5$ alkyl group or a metal ion for forming a non-toxic salt. When $R^1$ is an alkyl group, examples of such groups are methyl, ethyl, propyl, isopropyl, isobutyl, t-butyl and the like, and preferably, a methyl group is used. When $R^1$ is a hydrogen atom, a non-toxic salt thereof formed with an appropriate inorganic or organic base can be used. As such a base, inorganic bases such as, for example, hydroxides, carbonates, and bicarbonates of alkali metals or alkaline earth metals such as sodium, potassium, calcium, magnesium and the like and organic bases such as, for example, primary, secondary or tertiary alkylamines such as methylamine, dimethylamine, trimethylamine, ethylamine, diethylamine, triethylamine and the like; primary, secondary or tertiary alkanolamines such as ethanolamine, diethanolamine, triethanolamine and the like; diamines such as ethylenediamine, hexamethylenediamine and the like; cyclic saturated or unsaturated amines such as pyrrolidine, piperidine, morpholine, piperazine, N-methylmorpholine, pyridine and others can be used.

In the formula (I), $R^2$ and $R^3$ independently represent a hydrogen atom or —$OR^4$, where $R^4$ represents a hydrogen atom or a $C_1$-$C_3$ alkyl group such as methyl, ethyl or propyl group.

In the formula (I), A represents a group:

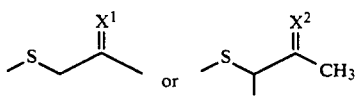

[where $X^1$ and $X^2$ represents an oxygen atom or $N-OR^5$ (where $R^5$ represents a hydrogen atom or a $C_1$-$C_3$ alkyl group)], a group:

[where $Y^1$ and $Y^2$ independently represent an oxygen atom or a group $N-OR^6$ (where $R^6$ represents a hydrogen atom or a $C_1$-$C_3$ alkyl group)], or a group:

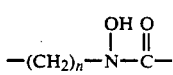

(where n is 0 or 1).

In the formula (I), B represents —$(CH_2)_m$— wherein m is an integer of 1 to 8, —$(CH_2)_{m1}$—O—$(CH_2)_{m2}$— wherein $m_1$ and $m_2$ are independently 1 or 2, or

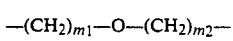

wherein $m_3$ is 0 or 1. The moiety —$(CH_2)_{m3}$— may be bonded to the aromatic ring at either the ortho, meta, or para position. The preferable position is a meta-substituted phenylene group.

The preferable naphthalene derivative thus has the formula (I) wherein, when $R^2$ is a hydrogen atom and $R^3$ is a hydrogen atom, a hydroxyl group, or a methoxy group, A is a group:

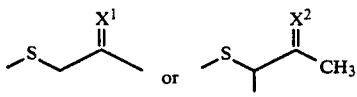

[where $X^1$ and $X^2$ are an oxygen atom or a group $N-OR^5$ (where $R^5$ is a hydrogen atom or a methyl group)] or a group:

[where $Y^1$ and $Y^2$ are independently an oxygen atom or a group $N-OR^6$ (where $R^6$ is a hydrogen atom or a methyl group)]. Furthermore, B is preferably —$(CH_2)_{m'}$— (where m' is an integer of 1 to 4). Furthermore, when $R^2$ is a hydrogen atom, a hydroxyl group, or a methoxy group, and when $R^3$ is a hydrogen atom, A is a group:

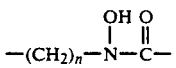

n is 0 or 1, and, more preferably, B is a group:

—$(CH_2)_{m''}$— where m'' is 2 to 5, or a methaphenylene group:

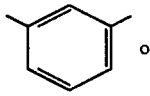 or a group:

—$CH_2$—O—$CH_2$—.

The present novel naphthalene derivatives [I] can be prepared as follows.

According to the first embodiment, a naphthalene derivative (or a sulfide ketone) having the formula (I-a):

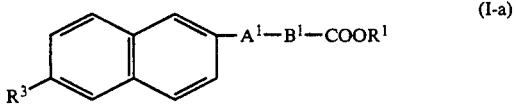 (I-a)

wherein $A^1$ represents a group

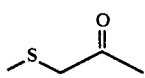

and $B^1$ represents —$(CH_2)_m$— where m is an integer of 1 to 8;

$R^1$ represents a hydrogen atom, a $C_1$-$C_5$ alkyl group or a non-toxic salt moiety, as mentioned above, $R^3$ represents a hydrogen atom or —$OR^4$, where $R^4$ represents a hydrogen atom or a $C_1$-$C_3$ alkyl group, as mentioned above can be prepared by reacting a thiol compound having the formula (II-a):

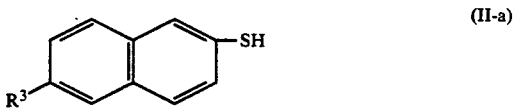 (II-a)

wherein $R^3$ is as defined above with a haloketone compound having the formula (III-a):

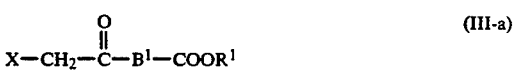 (III-a)

wherein X is a halogen atom such as Cl or Br and $R^1$ and $B^1$ are as defined above in the presence of a base or in a basic solvent.

According to the second embodiment, a naphthalene derivative (or a sulfide ketone) having the formula (I-b):

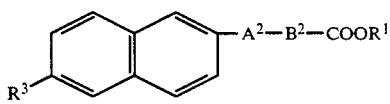 (I-b)

wherein A² represents a group

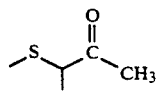

B² represents —(CH₂)ₘ—, where m is an integer of 1 to 8, and R¹ and R³ are as defined above, can be prepared by reacting a sulfide ketone compound having the formula (II-b):

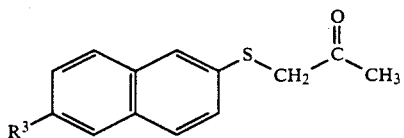 (II-b)

wherein R¹ is as defined above with a halogen compound having the formula (III-b):

 (III-b)

(where X represents a halogen atom (e.g., Cl or Br) and R¹ and B² are as defined above) in the presence of a base.

According to the third embodiment of the present invention, a naphthalene derivative (or a sulfide ketone) having the formula (I-c):

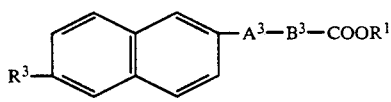 (I-c)

wherein A³ represents

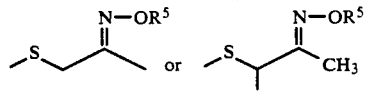

(where R⁵ represents a hydrogen atom or a methyl group);

B³ represents —(CH₂)ₘ— (where m is an integer to 8);

R¹ and R² are the same as defined above, can be prepared by reacting a sulfide ketone compound having the formula (I-c'):

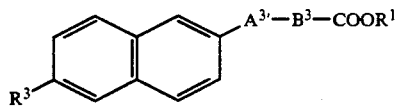 (I-c')

wherein A³' represents

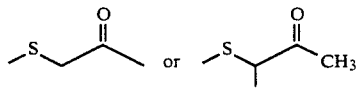

and R¹, R³ and B³ are as defined above with a hydroxylamine derivative having the formula (III-c) or a hydrochloride thereof $H_2N-OR^5$  (III-c)

wherein R⁵ is as defined above.

The compound represented by the formula (I-a) is obtained by reacting a thiol compound represented by the formula (II-a) with a haloketone compound represented by the formula (III-a) in the presence of a base or under a basic solvent. In the reaction between the thiol compound represented by the formula (II-a) and the haloketone compound represented by the formula (III-a), as the basic solvent, there may be included diethylamine, triethylamine, pyridine, ethylenediamine, pyrrolidine, and preferably pyridine is used. Various solid organic bases (e.g., 4-dimethylamino pyridine, 4-pyrrolidinopyridine) or inorganic bases (e.g., potassium carbonate, potassium bicardonate, sodium carbonate) can be used in the reaction. In this case, as the solvent to be used in the present invention, acetone, tetrahydrofuran, benzene, dimethylformamide may be included, and the reaction may be also carried out with an addition of water into the reaction system.

The haloketone compound (III-a) is preferably employed in an amount of 0.5 to 10-fold equivalents, more preferably 0.9 to 2.0-fold equivalents relative to the thiol compound (II-a), or when using a base, preferably used in an amount of 0.5 to 15-fold equivalents, more preferably 1.0 to 3.0-fold equivalents relative to the thiol compound (II-a). The reaction temperature is preferably from 0° to 150° C., more preferably from 20° to 120° C. The reaction time, which depends on the compounds, is preferably about 10 minutes to 24 hours. After completion of the reaction, the above-mentioned sulfideketone derivative can be obtained by a conventional post-treatment such as extraction or column chromatography.

The compound represented by the formula (I-b) can be obtained by reacting the sulfideketone compound represented by the formula (II-b) with the halogenic compound represented by the formula (III-b) in the presence of a base. As the base to be employed, bases such as sodium hydride, lithium diisopropylamide (LDA), etc., may be employed, but preferably sodium hydride is used. The solvent to be used in the reaction may include tetrahydrofuran, diethyl ether, dimethyl sulfoxide, benzene, etc., but preferably dimethylformamide is used.

The compound (III-b) is preferably employed in an amount of 0.5 to 10-fold equivalents, more preferably 0.9 to 5-fold equivalents, and the base is preferably used in an amount of 0.5 to 15-fold equivalents, more preferably 0.9 to 5-fold equivalents, relative to the sulfideketone compound (II-b). The reaction temperature is preferably from 0° to 100° C., more preferably from 20° to 80° C. The reaction time, which depends on the compounds, is preferably about 20 minutes to 24 hours. After completion of the reaction, the above-mentioned compound (I-b) is obtained by a conventional post-treatment such as extraction or column chromatography.

The compound represented by the formula (I-c) can be obtained by reacting the sulfideketone compound represented by the formula (I-c') with the hydroxylamine derivative represented by the formula (III-c) or a hydrochloride thereof. At this time, depending on the compounds, when an inorganic base such as sodium carbonate is used for the neutralization of the hydrochloride, good results may be obtained. The hydroxylamines (III-c) are preferably employed, relative to the sulfide ketone (the formula (I-c')), at 1.0 to 20-fold equivalents, more preferably 5.0 to 10-fold equivalents, and when an inorganic base is added, are preferably used in an amount of 0.5 to 1.0-fold equivalents relative to the hydroxylamines. The reaction solvent preferably can dissolve all of the compounds and can perform a uniform reaction, including, for example, binary systems of alcohol-water such as ethanol-water, methanol-water, etc. The reaction temperature is preferably from 0° to 100° C., more preferably from 20° to 50° C. The reaction time is preferably about 1 hour to 36 hours. After completion of the reaction, the sulfideketone derivative represented by the formula (I-c) is obtained by a conventional post-treatment such as extraction column chromatography.

The compound (I-c) can be then subjected to a hydrolysis reaction, if necessary. That is, the ester group in the formula (I) [COOR$^1$, R$^1$ is a C$_1$–C$_4$ lower alkyl group] can be subjected to a hydrolysis reaction. For such a hydrolysis reaction, a method known per se may be employed, such as the method in which a hydrolysis is carried out in the presence of a basic compound such as sodium hydroxide, potassium hydroxide, and lithium hydroxide, etc., thus giving the corresponding carboxylic acid derivative. The isolation purification of the desired product can be done by conventional methods, such as extraction or chromatography. The non-toxic salt of the carboxylic acid derivative can be obtained by a salt forming reaction, and the salt forming reaction can be performed by reacting the carboxylic acid obtained by the method as described above with, for example, hydroxides or carbonates of alkali metals, ammonium hydroxide, ammonium carbonate, ammonia or amine.

Specific examples of the compounds (I-a), (I-b), and (I-c) of the present invention include the following compounds.

(1-1) methyl 4-(6-methoxy-2-naphthylthio)-3-oxobutanoate
(1-2) methyl 5-(6-methoxy-2-naphthylthio)-6-oxoheptanoate
(1-3) methyl 5-(6-methoxy-2-naphthylthio)-6-hydroxyiminoheptanoate
(1-4) methyl 4-(6-hydroxy-2-naphthylthio)-3-oxobutanoate
(1-5) methyl 4-(6-methoxy-2-naphthylthio)-3-methoxyiminobutanoate
(1-6) methyl 4-(6-hydroxy-2-naphthylthio)-3-methoxyiminobutanoate
(1-7) methyl 5-(6-methoxy-2-naphthylthio)-4-oxopentanoate
(1-8) methyl 5-(6-methoxy-2-naphthylthio)-3-oxopentanoate
(1-9) methyl 5-(6-methoxy-2-naphthylthio)-4-hydroxyiminopentanoate
(1-10) methyl 5-(6-hydroxy-2-naphthylthio)-4-hydroxyiminopentanoate
(1-11) methyl 6-(6-hydroxy-2-naphthylthio)-5-oxohexanoate
(1-12) methyl 6-(6-hydroxy-2-naphthylthio)-5-hydroxyiminohexanoate
(1-13) methyl 6-(6-methoxy-2-naphthylthio)-5-oxohexanoate
(1-14) methyl 6-(6-methoxy-2-naphthylthio)-5-hydroxyiminohexanoate
(1-15) methyl 4-(2-naphthylthio)-3-oxobutanoate
(1-16) methyl 4-(2-naphthylthio)-3-methoxyiminobutanoate
(1-17) methyl 5-(2-naphthylthio)-4-oxopentanoate
(1-18) methyl 5-(2-naphthylthio)-4-methoxyiminopentanoate
(1-19) methyl 6-(2-naphthylthio)-5-oxohexanoate
(1-20) methyl 6-(2-naphthylthio)-5-methoxyiminohexanoate
(1-21) methyl 5-(2-naphthylthio)-4-hydroxyiminopentanoate
(1-22) methyl 6-(2-naphthylthio)-5-hydroxyiminohexanoate
(1-23) methyl 5-(6-hydroxy-2-naphthylthio)-6-oxoheptanoate
(1-24) methyl 5-(6-hydroxy-2-naphthylthio)-6-hydroxyiminoheptanoate
(1-25) methyl 5-(2-naphthylthio)-6-oxoheptanoate
(1-26) methyl 5-(2-naphthylthio)-6-hydroxyiminoheptanoate
(1-27) methyl 4-(6-methoxy-2-naphthylthio)-5-oxohexanoate
(1-28) methyl 4-(6-methoxy-2-naphthylthio)-5-hydroxyiminohexanoate
(1-29) methyl 4-(6-hydroxy-2-naphthylthio)-5-oxohexanoate
(1-30) methyl 4-(6-hydroxy-2-naphthylthio)-5-hydroxyiminohexanoate
(1-31) methyl 4-(2-naphthylthio)-5-oxohexanoate
(1-32) methyl 4-(2-naphthylthio)-5-hydroxyiminohexanoate
(1-33) methyl 3-(6-methoxy-2-naphthylthio)-4-oxopentanoate
(1-34) methyl 3-(6-methoxy-2-naphthylthio)-4-hydroxyiminopentanoate
(1-35) methyl 3-(6-hydroxy-2-naphthylthio)-4-oxopentanoate
(1-36) methyl 3-(6-hydroxy-2-naphthylthio)-4-hydroxyiminopentanoate
(1-37) methyl 3-(2-naphthylthio)-4-oxopentanoate
(1-38) methyl 3-(2-naphthylthio)-4-hydroxyiminopentanoate
(1-39) methyl 5-(6-hydroxy-2-naphthylthio)-6-methoxyiminoheptanoate
(1-40) methyl 5-(2-naphthylthio)-6-methoxyiminoheptanoate
(1-41) methyl 5-(6-methoxy-2-naphthylthio)-6-methoxyiminoheptanoate
(1-42) methyl 4-(6-methoxy-2-naphthylthio)-5-methoxyiminohexanoate
(1-43) methyl 4-(6-hydroxy-2-naphthylthio)-5-methoxyiminohexanoate
(1-44) methyl 4-(2-naphthylthio)-5-methoxyiminohexanoate
(1-45) methyl 3-(2-naphthylthio)-4-methoxyiminopentanoate
(1-46) methyl 3-(6-methoxy-2-naphthylthio)-4-methoxyiminopentanoate
(1-47) methyl 3-(6-hydroxy-2-naphthylthio)-4-methoxyiminopentanoate (1-48) carboxylic acid derivatives of the compound (1-1) to (1-47)
(1-49) ethyl ester derivatives of the compounds (1-48)
(1-50) sodium salts of the compounds (1-48).

According to the fourth embodiment of the present invention, a naphthalene derivative (or 1,2-diketone derivative) having the formula (I-d)

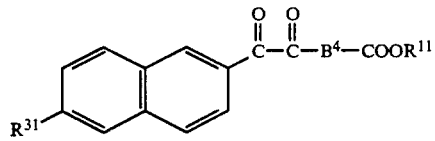
(I-d)

wherein $R^{11}$ represents a $C_1$–$C_5$ alkyl group;
$R^{31}$ represents —$OR^{41}$ (where $R^{41}$ is a $C_1$–$C_3$ alkyl group); and
$B^4$ represents $-(CH_2)_m-$ (where m is an integer of 1 to 8)
can be prepared by reacting a halogenated naphthyl compound having the formula (II-d):

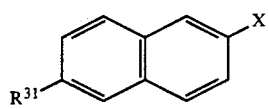
(II-d)

wherein X represents a halogen atom (e.g., Cl or Br) and $R^{31}$ is as defined above with an acetylene compound having the formula (III-d):

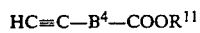

$HC\equiv C-B^4-COOR^{11}$ (III-d)

wherein $B^4$ and $R^{11}$ are as defined above in the presence of a metallic catalyst (e.g., Pd (II) and/or Cu (I)) in a basic solvent, followed by oxidizing the resultant acetylene derivative (IV):

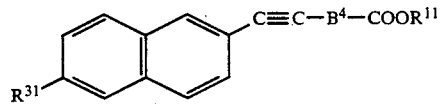
(IV)

wherein $R^{11}$, $R^{31}$, and $B^4$ are as defined above by $KM_nO_4$ as an oxidant.

According to the fifth embodiment of the present invention a naphthalene derivative (or 1,2-diketone derivative) having the formula (I-e):

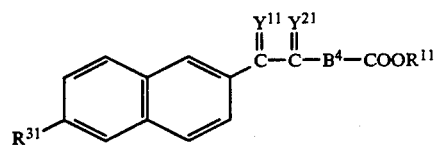
(I-e)

wherein $R^{11}$ represents a $C_1$–$C_5$ alkyl group;
$R^{31}$ represents —$OR^{41}$ (where $R^{41}$ is a $C_1$–$C_3$ alkyl group);
$B^4$ represents $-(CH_2)_m-$ (where m is an integer of 1 to 8), and
$Y^{11}$ and $Y^{12}$ independently represent an oxygen atom or a group N—$OR^6$ (where $R^6$ represents a hydrogen atom or a methyl group) provided that both $Y^{11}$ and $Y^{12}$ are not an oxygen atom can be prepared by reacting a 1,2-diketone derivative having the formula (I-d):

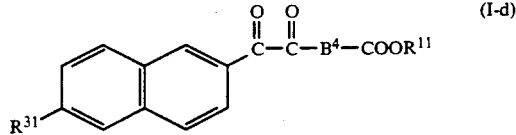
(I-d)

wherein $R^{11}$, $R^{31}$ and $B^4$ are as defined above with a hydroxylamine derivative (III-e) or a hydrochloride thereof:

$H_2N-OR^6$ (III-e)

wherein $R^6$ represents a hydrogen atom or a methyl group.

According to the sixth embodiment of the present invention, a naphthalene derivative (or 1,2-diketone derivative) having the formula (I-f):

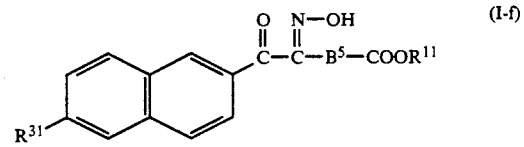
(I-f)

wherein $R^{11}$ represents a $C_1$–$C_5$ alkyl group;
$R^{31}$ represents —$OR^{41}$ (where $R^{41}$ is a $C_1$–$C_3$ alkyl group); and
$B_5$ represents —$(CH_2)_m$— (where m is an integer of 1 to 8)
can be prepared by reacting a naphthalene derivative (II-f):

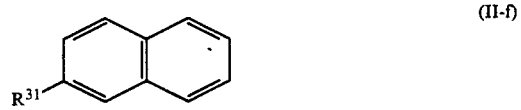
(II-f)

wherein $R^{31}$ is as defined above with an acid halide having the formula (III-f):

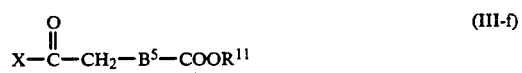
(III-f)

$$X-\overset{O}{\underset{\|}{C}}-CH_2-B^5-COOR^{11}$$

wherein X is a halogen atom (e.g., Cl or Br) and $R^{11}$ and $B^5$ are as defined above,
followed by reacting the resultant ketone derivative (V):

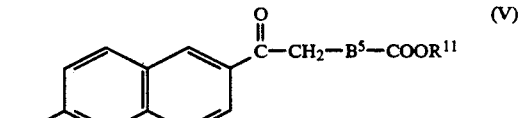
(V)

(wherein $R^{11}$, $R^{31}$ and $B^5$ are as defined above) with an alkali metal nitrite (e.g., $LiNO_2$ or $NaNO_2$).

The acetylene derivative represented by the formula [IV] can be obtained by reacting a halogenated naphthyl compound represented by the formula (II-d) with an acetylene compound represented by the formula (III-d) in the presence of a metal catalyst in a basic solvent.

Such a reaction may be carried out by using a catalytic amount of various metal complexes, for example, a Pd(0) complex such as Pd(PPh$_3$)$_4$, a Pd(II) complex such as PdCl$_2$(PhCN)$_2$, and alternatively, Ni(0), Ru(II), and Co(0) in a basic solvent such as ethylamine, diethylamine, triethylamine, pyridine, ethylenediamine, and pyrolidine. Preferably, PdCl$_2$(PPh$_3$)$_4$ and Cu(I) are employed as the catalyst and diethylamine as the solvent. The amounts thereof are preferably 0.001-fold equivalent to 0.5-fold equivalent, more preferably 0.01-fold to 0.1-fold, relative to the compound (II-d) for the metal catalyst, and 0.1-fold to 10-fold equivalent, more preferably 0.9-fold to 1.4-fold, for the acetylene compound (III-d). The reaction temperature is preferably from −50° C. to 150° C., more preferably from 10° C. to 60° C. The reaction time depends on the compounds, but is preferably about 10 minutes to 48 hours. After completion of the reaction, the basic solvent is evaporated and the residue then subjected to conventional post-treatment by extraction or column chromatography, to give the acetylene derivative (IV).

By then subjecting the acetylene derivative (IV) to an oxidation reaction by using an appropriate oxidizing agent, a 1,2-diketone derivative represented by the above formula (I-d) can be obtained. As the oxidizing agent to be used, for example, potassium permanganate, osmium tetraoxide, sodium dichromate, etc. may be included, but preferably potassium permanganate is used. The solvent to be used may be a solvent system which can dissolve both compounds, such as acetone-water or benzene-water, but in the case of a binary phase system, an interphase transfer catalyst such as tetrabutylammonium chloride is required.

The amount of the oxidizing agent is preferably 0.9 equivalents to 10 equivalents, more preferably 3 to 4 equivalents, relative to the acetylene derivative (IV), and when 0.4 to 0.6 equivalent of sodium bicarbonate is present, if 1.5 to 3 equivalents of anhydrous magnesium sulfate are added, better results are preferably obtained. The reaction temperature is preferably −50° C. to 80° C., more preferably about −10° to 40° C., and the reaction time is preferably 20 minutes to 24 hours, more preferably about 4 to 5 hours. After completion of the reaction, the oxidizing agent is removed, followed by a post-treatment such as extraction, column chromatography, to give the above 1,2-diketone derivative (I-d).

Also, by further reacting the 1,2-diketone derivative (I-d) with a hydroxylamine derivative represented by the formula (III-e), or a hydrochloride thereof, the 1,2-diketone derivative represented by the formula (I-e) can be obtained. At this time, depending on the compound, an inorganic base such as sodium carbonate may be employed for neutralizing the hydrochloride, to give good results. The hydroxylamine derivative or the hydrochloride (III-e) thereof employed relative to the 1,2-diketone derivative (I-d) to be reacted is preferably 1.0-fold to 20-fold equivalents, more preferably 5-fold to 10-fold equivalents, and when an inorganic base is used, preferably is used in an amount of 0.5-fold to 1-fold equivalent relative to the hydroxylamine derivative.

The reaction solvent preferably can dissolve all the compounds and perform a uniform reaction, as exemplified by a binary phase system of an alcohol-water system such as ethanol-water and methanol-water. The reaction temperature is preferably from 0° C. to 100° C., more preferably from 20° C. to 50° C. The reaction time is preferably, for example, about 1 to 36 hours. After completion of the reaction, the 1,2-diketone derivative (I-e) is obtained according to a conventional post-treatment such as extraction or column chromatography.

The ketone derivative represented by the formula (V) can be obtained by reacting a naphthalene represented by the formula (II-f) with an acid halide represented by the formula (III-f), by using a Lewis acid such as aluminum chloride.

The Lewis acid to be used is not limited to aluminum chloride, and Lewis acids in general, such as zinc chloride, trifluoroboron, sulfuric acid, etc., can be utilized. Relative to naphthalenes (II-f), the Lewis acids are preferably employed in an amount of 0.9 to 3.0-fold equivalents, more preferably 1.5-fold equivalents, and acid halides (III-f) 0.9 to 5.0-fold equivalents, most preferably 1.5-fold equivalents. As the reaction solvent, solvents such as carbon disulfide, carbon tetrachloride, and dichloromethane, nitrobenzene can be employed, but preferably nitrobenzene is used. The reaction temperature is preferably −20° C. to 100° C., more preferably −5° C. to 35° C., and the reaction time is preferably 15 minutes to 30 hours, more preferably about 1 hour to 12 hours. After completion of the reaction, the reaction mixture is poured onto ice-water, followed by a conventional post-treatment such as extraction or column chromatography, to give the ketone derivative (V).

Subsequently, by reacting the ketone derivative (V) with a nitrite of an alkali metal, the 1,2-diketone derivative represented by the formula (I-f) is obtained. As the nitrite of an alkali metal to be used in this reaction, nitrites of sodium or lithium may be included. For the reaction, preferably a hydrogen halide such as hydrochloric acid or hydrobromic acid, more preferably hydrochloric acid, is employed, in an amount of 1.0-fold to 30-fold equivalents, more preferably 5.0 to 15-fold equivalents, relative to the ketone derivative (V). The nitrite of an alkali metal is preferably employed in an amount of 0.9 to 15-fold equivalents, more preferably 1.0 to 2.0-fold equivalents, and as the reaction solvent, a $C_1$ to $C_4$ lower alcohol, preferably an alcohol corresponding to $R^{11}$ of the ester moiety of the ketone derivative (V), is employed. The reaction temperature is preferably −20° C. to 80° C., more preferably 0° C. to 30° C., and the reaction time is preferably 15 minutes to 30 hours, more preferably 1 hour to 15 hours. After the completion of the reaction, the reaction mixture is neutralized with a saturated aqueous solution of an inorganic base such as sodium bicarbonate, followed by a conventional post-treatment such as extraction or column chromatography, to give the 1,2-diketone derivative represented by the above formula (I-f).

Specific examples of the 1,2-diketone derivative of the present invention include the following compounds.

(2-1) methyl 6(6-methoxy-2-naphthyl)-5,6-dioxohexanoate (2-2) methyl 6(6-methoxy-2-naphthyl)-5-hydroxyimino-6-oxohexanoate (2-3) methyl 6(6-methoxy-2-naphthyl)-5-methoxyimino-6-oxohexanoate (2-4) methyl 6(6-methoxy-2-naphthyl)-5,6-dihydroxyiminohexanoate (2-5) methyl 6(6-methoxy-2-naphthyl)-5,6-dioxohexanoate (2-6) methyl 6(6-hydroxy-2-naphthyl)-5,6-dioxohexanoate (2-7) methyl 6(6-hydroxy-2-naphthyl)-5-hydroxyimino-6-oxohexanoate (2-8) methyl 6(6-hydroxy-2-naphthyl)-5-methoxyimino-6-oxohexanoate
(2-9) methyl 6(6-hydroxy-2-naphthyl)-5,6-dihydroxyiminohexanoate
(2-10) methyl 6(6-hydroxy-2-naphthyl)-5,6-dimethoxyiminohexanoate
(2-11) methyl 6(2-naphthyl)-5,6-dioxohexanoate
(2-12) methyl 6(2-naphthyl)-5-hydroxyimino-6-oxohexanoate
(2-13) methyl 6(2-naphthyl)-5-methoxyimino-6-oxohexanoate
(2-14) methyl 6(2-naphthyl)-5,6-dihydroxyiminohexanoate
(2-15) methyl 6(2-naphthyl)-5,6-dimethoxyiminohexanoate
(2-16) carboxylic acid derivatives of the compounds (2-1) to (2-15)
(2-17) ethyl ester derivatives of the compounds (2-1) to (2-15)
(2-18) sodium salts of the compounds (16).

According to the seventh embodiment of the present invention, a naphthalene derivative (or 1,2-hydroxamic acid derivative) having the formula (I-g):

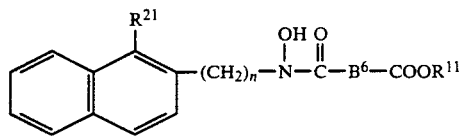

wherein $R^{11}$ represents a $C_1$-$C_5$ alkyl group;
$R^{21}$ represents —$OR^{41}$ (where $R^{41}$ is a $C_1$-$C_3$ alkyl group);
$B^6$ represents —$(CH_2)_m$— (where m is an integer of 1 to 8), —$(CH_2)_{m1}$—O—$(CH_2)_{m2}$— (where $m_1$ and $m_2$ are independently 1 or 2), or

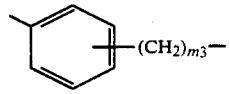

(where $m_3$ is 0 or 1); and
n is 0 or 1
can be prepared by reacting a hydroxyamine derivative (II-g) or a hydrochloride thereof:

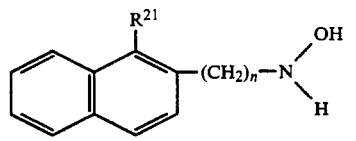

wherein $R^{21}$ and n are as defined above
with an acid chloride compound (III-g):

ClOC—$B^6$—COOR$^{11}$(III-g)

wherein $R^{11}$ and $B^6$ are as defined above in the presence of a base.

The reaction between the compound of the formula (II-g) and the compound of the formula (III-g) may be carried out by adding an acid chloride represented by the formula (III-g) to a mixture of a hydroxylamine derivative (II-g) or a hydrochloride compound thereof and a base, for example, an organic base such as triethylamine, pyridine, and 4-dimethylaminopyridine, or an inorganic base such as sodium carbonate and sodium hydrogen carbonate, but the base used in this reaction is not limited to those mentioned above. As the solvent to be used in the present invention, for example, methylene chloride, carbon tetrachloride, tetrahydrofuran, diglyme, dimethylformamide, dimethyl sulfoxide, benzene, or a solvent mixture thereof may be employed, and the reaction may be carried out with an addition of water to the reaction system.

Relative to the hydroxylamine derivative (II-g), the base may be employed in an amount of 0.1 to 10-fold equivalents, preferably 0.9 to 1.4 equivalents, and the acid chloride compound (III-g) in an amount of 0.1 to 10-fold equivalents, preferably 0.9 to 1.4-fold equivalents. The reaction temperature is preferably from 0° C. to 150° C., more preferably from 10° C. to 80° C. The reaction time depends on the compounds, but is preferably about 10 minutes to 24 hours. After completion of the reaction, the above-mentioned hydroxamic acid derivative (I-g) is obtained according to a conventional post-treatment such as extraction or column chromatography.

Such a hydroxamic acid derivative can be subsequently subjected to a hydrolysis reaction, if necessary. That is, the ester group [COOR$^{11}$] in the formula (I-g) can be subjected to a hydrolysis reaction, and such a hydrolysis reaction can be carried out according to the known method per se, for example, the method in which the hydrolysis is effected in the presence of a basic compound such as sodium hydroxide, potassium hydroxide, and lithium hydroxide, to thus give the corresponding carboxylic acid derivative.

The isolation purification of the desired product can be performed by conventional methods, namely by means such as extraction, chromatography, and recrystallization. Non-toxic salts of carboxylic acid derivatives are obtained by salt forming reactions, and such salt forming reactions may be carried out by reacting the carboxylic acid obtained by the method as described above with bases as mentioned above, such as hydroxides or carbonates of alkali metals, ammonium hydroxide, ammonium carbonate, ammonia or amines.

The hydroxylamine derivative (II-g) to be used for the synthesis of the hydroxamic acid derivative can be synthesized according to the method known per se, for example, according to the following route.

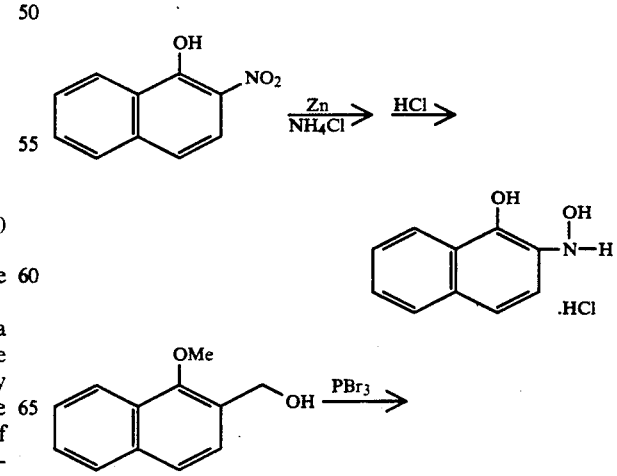

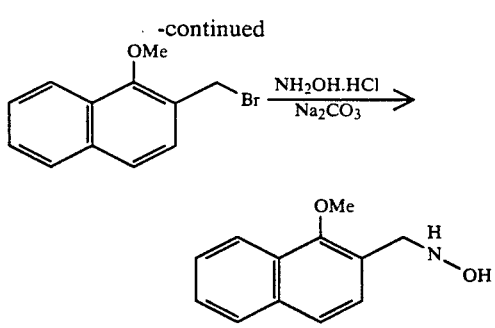

Specific examples of the naphthalene derivative of the present invention include the following compounds.

(3-1) N-hydroxy-N-(1-hydroxy-2-naphthyl)-3-methoxycarbonylpropionamide
(3-2) N-hydroxy-N-(1-hydroxy-2-naphthyl)-4-methoxycarbonylbutanamide
(3-3) N-hydroxy-N-(1-hydroxy-2-naphthyl)-5-methoxycarbonylpentanamide
(3-4) N-hydroxy-N-(1-hydroxy-2-naphthyl)-6-methoxycarbonylhexanamide
(3-5) N-hydroxy-N-(1-methoxy-2-naphthyl)-3-methoxycarbonylpropionamide
(3-6) N-hydroxy-N-(1-methoxy-2-naphthyl)-4-methoxycarbonylbutanamide
(3-7) N-hydroxy-N-(1-methoxy-2-naphthyl)-5-methoxycarbonylpentanamide
(3-8) N-hydroxy-N-(1-methoxy-2-naphthyl)-6-methoxycarbonylhexanamide
(3-9) N-hydroxy-N-(2-naphthyl)-3-methoxycarbonylpropionamide
(3-10) N-hydroxy-N-(2-naphthyl)-4-methoxycarbonylbutanamide
(3-11) N-hydroxy-N-(2-naphthyl)-5-methoxycarbonylpentanamide
(3-12) N-hydroxy-N-(2-naphthyl)-6-methoxycarbonylhexanamide
(3-13) N-hydroxy-N-(1-hydroxy-2-naphthylmethyl)-3-methoxycarbonylpropionamide
(3-14) N-hydroxy-N-(1-hydroxy-2-naphthylmethyl)-4-methoxycarbonylbutanamide
(3-15) N-hydroxy-N-(1-hydroxy-2-naphthylmethyl)-5-methoxycarbonylpentanamide
(3-16) N-hydroxy-N-(1-hydroxy-2-naphthylmethyl)-6-methoxycarbonylhexanamide
(3-17) N-hydroxy-N-(1-methoxy-2-naphthylmethyl)-3-methoxycarbonylpropionamide
(3-18) N-hydroxy-N-(1-methoxy-2-naphthylmethyl)-4-methoxycarbonylbutanamide
(3-19) N-hydroxy-N-(1-methoxy-2-naphthylmethyl)-5-methoxycarbonylpentanamide
(3-20) N-hydroxy-N-(1-methoxy-2-naphthylmethyl)-6-methoxycarbonylhexanamide
(3-21) N-hydroxy-N-(2-naphthylmethyl)-3-methoxycarbonylpropionamide
(3-22) N-hydroxy-N-(2-naphthylmethyl)-4-methoxycarbonylbutanamide
(3-23) N-hydroxy-N-(2-naphthylmethyl)-5-methoxycarbonylpentanamide
(3-24) N-hydroxy-N-(2-naphthylmethyl)-6-methoxycarbonylhexanamide
(3-25) N-hydroxy-N-(1-hydroxy-2-naphthyl)-3-methoxycarbonylbenzamide
(3-26) N-hydroxy-N-(1-hydroxy-2-naphthyl)-2-methoxycarbonylbenzamide
(3-27) N-hydroxy-N-(1-hydroxy-2-naphthyl)-4-methoxycarbonylbenzamide
(3-28) N-hydroxy-N-(1-hydroxy-2-naphthyl)-3-methoxycarbonylmethylbenzamide
(3-29) N-hydroxy-N-(1-hydroxy-2-naphthyl)-2-methoxycarbonylmethylbenzamide
(3-30) N-hydroxy-N-(1-hydroxy-2-naphthyl)-4-methoxycarbonylmethylbenzamide
(3-31) N-hydroxy-N-(1-hydroxy-2-naphthyl)-3-methoxycarbonylphenylacetamide
(3-32) N-hydroxy-N-(1-hydroxy-2-naphthyl)-2-methoxycarbonylphenylacetamide
(3-33) N-hydroxy-N-(1-hydroxy-2-naphthyl)-4-methoxycarbonylphenylacetamide
(3-34) N-hydroxy-N-(1-methoxy-2-naphthyl)-3-methoxycarbonylbenzamide
(3-35) N-hydroxy-N-(1-methoxy-2-naphthyl)-2-methoxycarbonylbenzamide
(3-36) N-hydroxy-N-(1-methoxy-2-naphthyl)-4-methoxycarbonylbenzamide
(3-37) N-hydroxy-N-(1-methoxy-2-naphthyl)-3-methoxycarbonylmethylbenzamide
(3-38) N-hydroxy-N-(1-methoxy-2-naphthyl)-2-methoxycarbonylmethylbenzamide
(3-39) N-hydroxy-N-(1-methoxy-2-naphthyl)-4-methoxycarbonylmethylbenzamide
(3-40) N-hydroxy-N-(1-methoxy-2-naphthyl)-3-methoxycarbonylphenylacetamide
(3-41) N-hydroxy-N-(1-methoxy-2-naphthyl)-2-methoxycarbonylphenylamide
(3-42) N-hydroxy-N-(1-methoxy-2-naphthyl)-4-methoxycarbonylphenylacetamide
(3-43) N-hydroxy-N-(2-naphthyl)-3-methoxycarbonylbenzamide
(3-44) N-hydroxy-N-(2-naphthyl)-2-methoxycarbonylbenzamide
(3-45) N-hydroxy-N-(2-naphthyl)-4-methoxycarbonylbenzamide
(3-46) N-hydroxy-N-(2-naphthyl)-3-methoxycarbonylmethylbenzamide
(3-47) N-hydroxy-N-(2-naphthyl)-2-methoxycarbonylmethylbenzamide
(3-48) N-hydroxy-N-(2-naphthyl)-4-methoxycarbonylmethylbenzamide
(3-49) N-hydroxy-N-(2-naphthyl)-3-methoxycarbonylphenylacetamide
(3-50) N-hydroxy-N-(2-naphthyl)-2-methoxycarbonylphenylacetamide
(3-51) N-hydroxy-N-(2-naphthyl)-4-methoxycarbonylphenylacetamide
(3-52) N-hydroxy-N- 1-hydroxy-2-naphthyl)-4-methoxycarbonyl-3-oxabutanamide
(3-53) N-hydroxy-N-(1-methoxy-2-naphthyl)-4-methoxycarbonyl-3-oxabutanamide
(3-54) N-hydroxy-N-(2-naphthyl)-4-methoxycarbonyl-3-oxabutanamide
(3-55) N-hydroxy-N-(1-hydroxy-2-naphthylmethyl)-4-methoxycarbonyl-3-oxabutanamide
(3-56) N-hydroxy-N-(1-methoxy-2-naphthylmethyl)-4-methoxycarbonyl-3-oxabutanamide
(3-57) N-hydroxy-N-(2-naphthylmethyl)-4-methoxycarbonyl-3-oxabutanamide
(3-58) carboxylic acid derivatives of (3-1) to (3-57)
(3-59) sodium salt of (3-58)
(3-60) potassium salt of (3-58).

The aromatic derivatives in the present invention thus obtained were found to exhibit an inhibitory activity against lipoxygenase, and have an anti-SRS-A activity.

The naphthalene derivatives according to the present invention also were found to exhibit an inhibitory activity against lipoxygenase, and have an anti-SRS-A activity. Therefore, the compounds of the present invention are useful for the therapy or prophylaxis of allergic diseases such as bronchial asthma, nasal allergy, allergic opthalmia, and atopic dermatitis, etc., edema, iscemic diseases, circulatory diseases such as hypertension, ischemic cerebral disorder, etc. or psoriasis, and for the therapy or prophylaxis of viral diseases.

EXAMPLES

The present invention will now be further illustrated by, but is by no means limited to, the following Examples.

EXAMPLE 1-1

Synthesis of methyl 4-(6-methoxy-2-naphthyl)-3-oxobutanoate

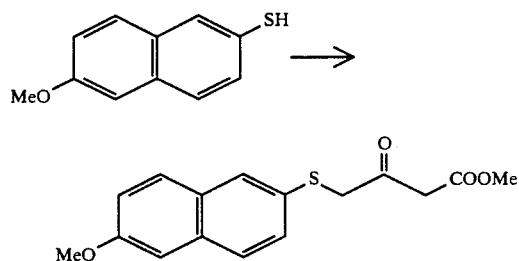

A solution of 154 mg (0.81 mmol) of 6-methoxynaphthalene-2-thiol in 5 ml of pyridine was ice-cooled, and 94 μl (0.81 mmol) of methyl chloroacetoacetate was added, followed by stirring at room temperature for 20 minutes. Further, the reaction was carried out at about 100° C. for one hour on an oil bath, dilute hydrochloric acid was added to complete the reaction, and the mixture was extracted with ether. The organic layer was dried over anhydrous magnesium sulfate, the solvent was removed under a reduced pressure, and the desired sulfide ketone derivative was obtained by silica gel column chromatography. Yield: 123 mg (50%).

$^1$H-NMR (90 MHz, CDCl$_3$) δ/ppm 3.64 (s, 2H), 3.66 (s, 3H), 3.82 (s, 2H), 3.88 (s, 3H), 7.07–7.26 (m, 6H).

$^{13}$C-NMR (22.5 MHz, CDCl$_3$) δ/ppm 44.50, 46.28, 52.23, 55.19, 105.66, 119.32, 127.62, 128.06, 128.39, 128.73, 128.97, 129.34, 133.51, 157.89, 167.19, 197.44

IR (neat) 1750 cm$^{-1}$ (νC=O), 1720 cm$^{-1}$ (νC=O)

Mass (EI) m/e=304 (M+)

EXAMPLE 1-2

Synthesis of 1-(6-methoxy-2-naphthylthio)-2-oxoprooane

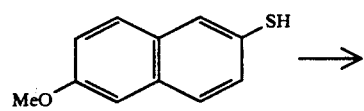

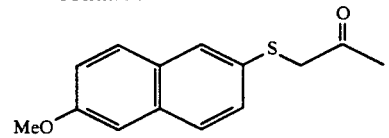

An amount of 1.004 g (5.26 mmol) of 6-methoxynaphthalene-2-thiol, 1.78 g (12.9 mmol) of potassium carbonate and 60 ml of acetone were mixed and stirred under an ice bath.

An amount of 0.72 ml (8.57 mmol) of bromoacetone was gradually added, and the mixture was stirred at room temperature for 1 hour and 45 minutes.

After removal of the potassium carbonate by filtration, acetone was evaporated under a reduced pressure, and the desired sulfideketone derivative was obtained by silica gel column chromatography. Yield: 763 mg (59%).

m.p. 74.5°–76.0° C.

$^1$H-NMR (90 MHz, CDCl$_3$) δ/ppm 2.28 (s, 3H), 3.71 (s, 2H), 3.91 (s, 3H), 7.08–7.74 (m, 6H).

EXAMPLE 1-3

Synthesis of methyl 5-(6-methoxy-2-naphthylthio)-6-oxoheptanoate

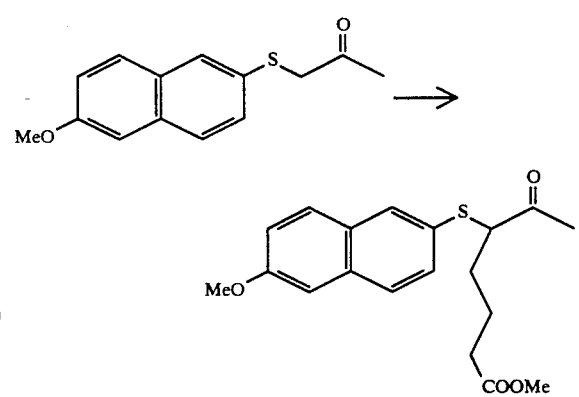

Into a solution of 237 mg (0.96 mmol) of 1-(6-methoxy-2-naphthylthio)-2-oxopropane in 5 ml of dry dimethylformamide was charged 53 mg (60% in oil, 1.33 mmol) of sodium hydride, and the mixture was stirred.

After 20 minutes, a solution of 202 mg (1.12 mmol) of methyl 4-bromobutyrate in 2 ml of dimethylformamide was gradually added, the mixture was stirred by heating at 60° C. for 3 hours, the reaction was completed by an addition of dil. hydrochloric acid, and the mixture was extracted with ethyl acetate. The organic layer was dried over anhydrous magnesium sulfate, the solvent was evaporated under a reduced pressure, and the sulfide ketone derivative of the desired product was obtained by silica gel column chromatography. Yield: 90 mg (25%).

$^1$H-NMR (90 MHz, CDCl$_3$) δ/ppm 1.64–1.93 (m, 4H), 2.27 (s, 3H), 2.14–2.34 (m, 2H), 3.64 (br, s, 4H), 3.89 (s, 3H), 7.08–7.80 (m, 6H).

$^{13}$C-NMR (22.5 MHz, CDCl$_3$) δ/ppm 22.58, 27.00, 29.50, 33.48, 51.47, 55.25, 57.61, 105.62, 119.29, 126.61, 127.43, 128.94, 128.97, 130.59, 132.45, 134.00, 158.12, 173.18, 204.43.

IR (neat) 1710 cm$^{-1}$ (νC=O) 1740 cm$^{-1}$ (νC=O)

Mass (EI) m/e=346 (M+)

EXAMPLE 1-4

Synthesis of methyl 5-(6-methoxy-2-naphthylthio1-6-hydroxyiminoheptanoate

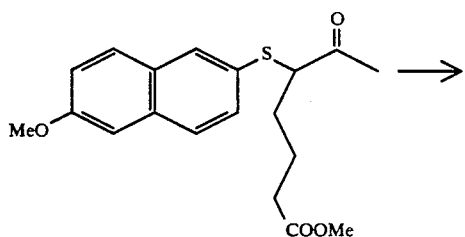

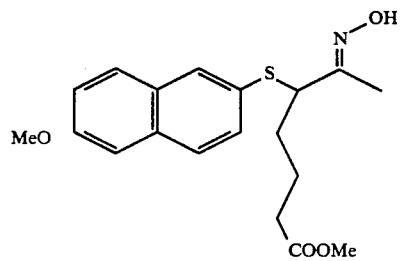

To 8.4 mg (0.12 mmol) of hydroxylamine hydrochloride was added a small amount of water, and an ethanolic solution of 20 mg (0.058 mmol) of methyl 5-(6-methoxy-2-naphthylthio)-6-oxoheptanoate was added thereto chilled with an ice bath, followed by stirring. At this time, insolubles were precipitated, and water and ethanol were added so that the reaction could proceed uniformly. After stirring at room temperature for 4 hours, the mixture was heated at 60° C. for 15 minutes.

The mixture was extracted with ether, and the desired sulfide ketone derivative was obtained by thin layer chromatography. Yield: 11.2 mg (54%).

$^1$H-NMR (90 MHz, CDCl$_3$) δ/ppm 1.73-1.90 (m, 4H), 1.96 (s, 3H), 2.27-2.40 (m, 2H), 3.66 (s, 3H), 3.89 (s, 3H), 6.3-6.4 (br, 6H), 7.05-7.78 (m, 6H).

EXAMPLE 1-5

Synthesis of methyl 4-(6-hydroxy-2-naphthylthio)-3-oxobutanoate

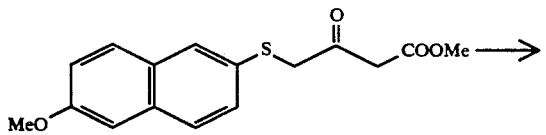

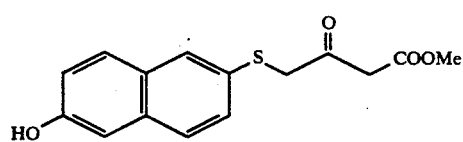

A dry methylene chloride solution of 102.8 mg (0.34 mmol) of 4-(6-methoxy-2-naphthylthio)-3-oxobutanoate was cooled to −78° C., one hundred (100) μl (0.97 mmol) of boron tribromide was added, and the reaction was carried out from −78° C. to room temperature for 2 hours. Then dry methanol (3 ml) was added, and the mixture was stirred over one day and night at room temperature. The mixture was extracted with ethyl acetate, and the organic layer was washed with saturated aqueous sodium chloride, followed by drying over anhydrous magnesium sulfate. The solvent was evaporated under a reduced pressure, and the desired sulfideketone derivative was obtained by silica gel column chromatography. Yield: 81.8 mg (83%).

$^1$H-NMR (90 MHz, CDCl$_3$) δ/ppm 3.67 (s, 3H), 3.70 (s, 2H), 3.79 (s, 2H), 5.6-6.4 (br, 1H), 6.92-7.70 (m, 6H).

EXAMPLE 1-6

Synthesis of methyl 4-(6-methoxy-2-naphthylthio)-3-methoxyiminobutanoate

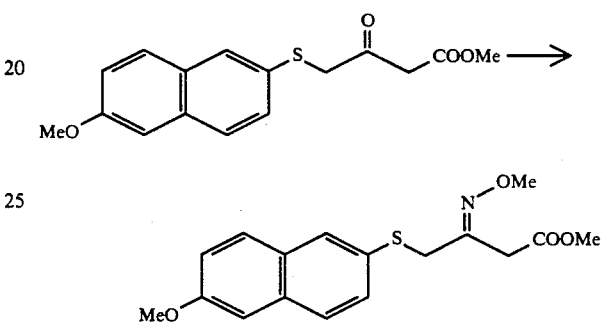

Into 60 mg (0.20 mmol) of 4-(6-methoxy-2-naphthylthio)-3-oxobutanoate, 25 mg (0.30 mmol) of o-methylhydroxylamine hydrochloride and 12.4 mg (0.15 mmol) of sodium carbonate were added appropriate amounts of ethanol and water, and the mixture was stirred at room temperature overnight so that the reaction mixture became uniform.

Saturated aqueous sodium chloride was added to the reaction mixture, the mixture was extracted with ether, and ether was evaporated under a reduced pressure to give 70 mg of the crude product.

The same reaction was carried out without an addition of sodium carbonate, and in this case, 68 mg of the crude product was obtained. These products were combined, and the desired sulfide ketone derivative was obtained by silica gel column chromatography. Yield: 79 mg (40%).

$^1$H-NMR (90 MHz, CDCl$_3$) (syn-, anti-mixture) 3.51, 3.36 (s, 2H), 3.66 (s, 3H), 3.73 (s, 3H), 3.82, 3.98 (s, 2H), 3.91 (s, 3H), 7.09 (m, 6H, Ar).

IR (neat) 1740 cm$^{-1}$ (νC=O), 1625 cm$^{-1}$ (νC=N)

Mass (EI) m/e=333 (M+)

EXAMPLE 1-7

Synthesis of methyl 4-(6-hydroxy-2-naphthylthio)-3-methoxyiminobutanoate

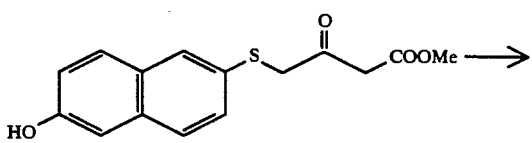

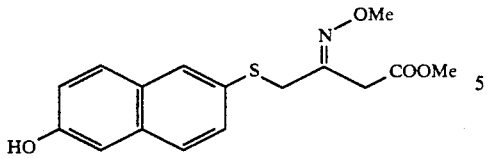

An amount of 85 mg (0.29 mmol) of methyl 4-(6-hydroxy-2-naphthylthio)-3-oxobutanoate, 33 mg (0.40 mmol) of o-methylhydroxylamine and 17 mg (0.20 mmol) of sodium carbonate were formed into a uniform solution with an addition of appropriate amounts of ethanol and water (each about 2 to 3 ml), and the mixture was stirred at room temperature for 2 hours. The mixture was extracted with ethyl acetate, and after evaporation of the solvent under a reduced pressure, the desired sulfide ketone derivative was obtained by silica gel column chromatography. Yield: 55 mg (56%).

¹H-NMR (90 MHz, CDCl₃) (syn-, anti-mixture) 3.37, 3.52 (s, 2H), 3.67 (s, 3H), 3.73 (s, 3H), 3.81, 3.98 (s, 2H), 5.60 (br, 1H), 7.00–7.79 (m, 6H).

EXAMPLE 1-8

Synthesis of methyl 5-(6-methoxy-2-naphthylthio)-4-oxopentanoate

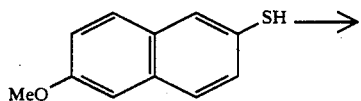

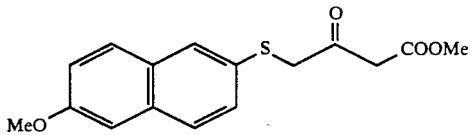

To a stirred solution of 304 mg (1.6 mmol) of 6-methoxynaphthalene-2-thiol in 10 ml of pyridine under an ice bath, a solution of 342 mg (1.64 mmol) of methyl 5-bromolevulinate in 2 ml of pyridine was added at once, and the mixture was stirred under ice bath for 20 minutes and then heated to about 100° C. for 40 minutes. After cooling to room temperature, the mixture was neutralized by an addition of dil. hydrochloric acid, extracted with ethyl acetate, the organic layer was dried over anhydrous magnesium sulfate, and after evaporation of the solvent under a reduced pressure, the desired sulfide ketone derivative was obtained by silica gel column chromatography. Yield: 255 mg (50%).

¹H-NMR (90 MHz, CDCl₃) δ/ppm 2.53 (t, 2H, J=6.5 Hz), 2.87 (t, 2H, J=6.5 Hz), 3.60 (s, 3H), 3.73 (s, 2H), 3.84 (s, 3H), 7.04–7.73 (m, 6H).

EXAMPLE 1-9

Synthesis of methyl 5-(6-hydroxy-2-naphthylthio)-4-oxopentanoate

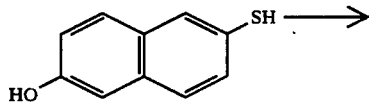

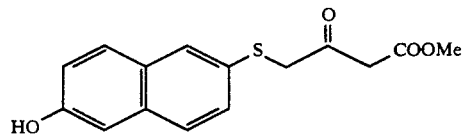

An amount 104 mg (0.59 mmol) of 6-hydroxynaphthalene-2-thiol and 5 ml of pyridine were stirred under an ice bath, a solution of 130 mg (0.62 mmol) of methyl 5-bromolevulinate in 2 ml of pyridine was added under an ice bath, and stirred as such for 1 hour, the mixture was neutralized by an addition of dilute hydrochloric acid and extracted with ethyl acetate, the organic layer was dried over anhydrous magnesium sulfate, and after the organic solvent was concentrated under a reduced pressure, the desired sulfide ketone derivative was obtained by silica gel column chromatography. Yield: 79 mg (44%).

¹H-NMR (90 MHz, CDCl₃) δ/ppm 2.52 (t, 2H, J=6.5 Hz), 2.96 (t, 2H, J=6.5 Hz), 3.57 (s, 3H), 3.91 (s, 2H), 7.10–7.97 (m, 6H), 8.60 (br, 1H).

EXAMPLE 1-10

Synthesis of methyl 5-(6-methoxy-2-naohthylthio)-4-hydroxyiminopentanoate

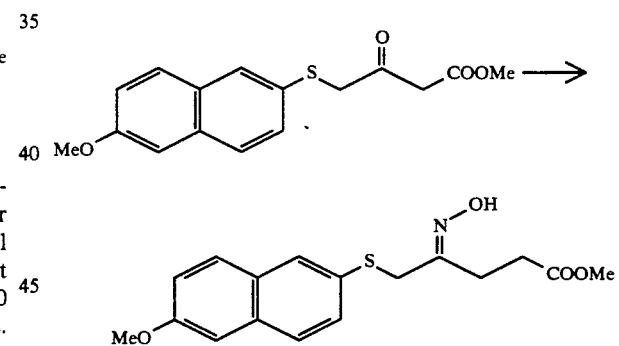

An amount 45 mg (0.14 mmol) of 5-(6-methoxy-2-naphthylthio)-4-oxopentanoate, 14 mg (0.20 mmol) of hydroxyamine hydrochloride and 12 mg (0.11 mmol) of sodium carbonate were dissolved in each about 2 ml of ethanol and water to become uniform, and the reaction was carried out at room temperature overnight, and by heating to about 60° C. overnight. The mixture was extracted with ether, washed with saturated aqueous sodium chloride, and then the organic layer was dried over anhydrous magnesium sulfate. The solvent was evaporated under a reduced pressure, and the desired sulfide ketone derivative was obtained by silica gel column chromatography. Yield: 27 mg (57%).

¹H-NMR (90 MHz, CDCl₃) δ/ppm (cis, trans mixture) 2.51–2.75 (m, 4H), 3.61, 3.66 (s, 3H), 3.85, 3.70 (s, 2H), 3.89 (s, 3H), 7.06–7.80 (m, 7H).

EXAMPLE 1-11

Synthesis of methyl 5-(6-hydroxy-2-naphthylthio)-4-hydroxyiminopentanoate

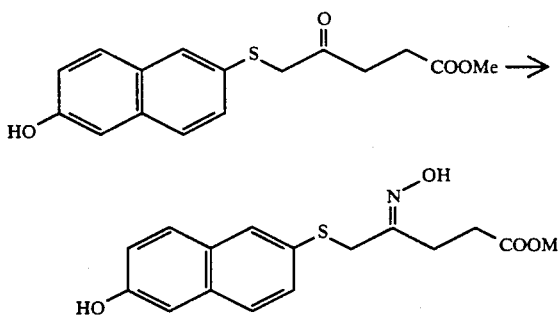

An amount 41 mg (0.13 mmol) of methyl-5-(6-hydroxy- 2-naphthylthio)-4-oxopentanoate and 14 mg (0.20 mmol) of hydroxylamine hydrochloride were dissolved in an ethanol-water solvent mixture (each about 4 ml), and the solution was stirred at room temperature overnight. The solution was extracted with ether, and the organic layer dried over anhydrous magnesium sulfate. The solvent was evaporated under a reduced pressure, and the desired sulfide ketone derivative was obtained by silica gel column chromatography. Yield: 25 mg (58%).

$^1$H-NMR (90 MHz, CDCl$_3$) δ/ppm (cis, trans mixture) 2.51-2.78 (m, 4H), 3.65, 3.87 (s, 2H), 3.67, 3.60 (s, 3H), 6.49-7.71 (m, 8H).

EXAMPLE 1-12

Synthesis of methyl 6-(6-hydroxy-2-naphthylthio)-5-oxohexanoate

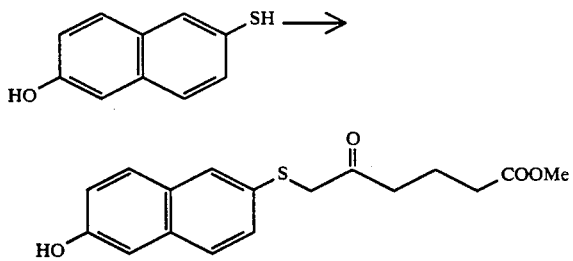

Into 205 ml (1.16 mmol) of 6-hydroxynaphthalene-2-thiol was charged 5 ml of pyridine, and the mixture was stirred under an ice bath. A solution of 315 mg of methyl 6-bromo-5-oxohexanoate in 2 ml of pyridine was added, and the mixture was stirred under an ice bath for 1 hour. Further, the reaction was carried out at room temperature for 4 hours, by heating to 90° C. for 4 hours, and subsequently stirring was continued at room temperature overnight. The reaction mixture was neutralized with dilute hydrochloric acid and extracted with ethyl acetate, and the organic layer was dried over anhydrous magnesium sulfate.

The solvent was evaporated under a reduced pressure, and the desired sulfide ketone derivative was obtained by silica gel column chromatography. Yield: 170 mg (46%).

$^1$H-NMR (90 MHz, CDCl$_3$) δ/ppm 1.89 (tt, 2H, J=7.3 Hz, 6.8 Hz), 2.32 (t, 2H, J=6.8Hz), 2.72 (t, 2H, J=7.3 Hz), 3.64 (s, 3H), 3.68 (s, 2H), 6.09 (brs, 1H), 6.95-7.73 (m, 6H).

EXAMPLE 1-13

Synthesis of methyl 6-(6-hydroxy-2-naphthylthio)-5-hydroxyiminohexanoate

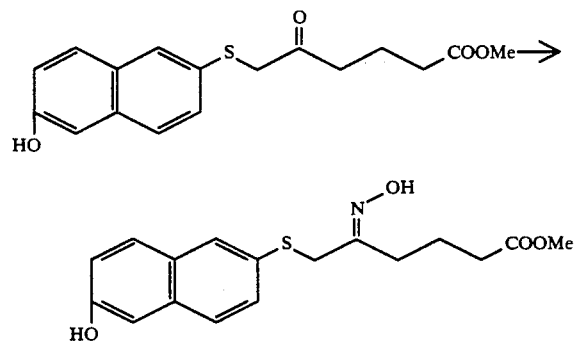

Into 32 mg (0.10 mmol) of 6-(6-hydroxy-2-naphthylthio)-5-oxohexanoate and 10 mg (0.14 mmol) of hydroxylamine hydrochloride were added an ethanol-water solvent mixture (each about 5 ml) to dissolve the compounds, and the solution was stirred at room temperature for one day and night. The mixture was extracted with ethyl acetate, the organic layer dried over anhydrous magnesium sulfate, the solvent was removed under a reduced pressure, and the desired sulfide ketone derivative was obtained by silica gel column chromatography. Yield: 15 mg (44%).

$^1$H-NMR (90 MHz, d$_6$-acetone) δ/ppm (cis-trans mixture) 1.72-2.09 (m, 2H), 2.21-2.62 (m, 4H), 3.57, 3.60 (s, 3H), 3.93, 3.74 (s, 2H), 7.07-7.82 (m, 6H), 8.59 (brs, 1H), 9.90, 9.72 (brs, 1H).

EXAMPLE 1-14

Synthesis of 6-(6-hydroxy-2-naphthylthio)-5-oxohexanoic acid

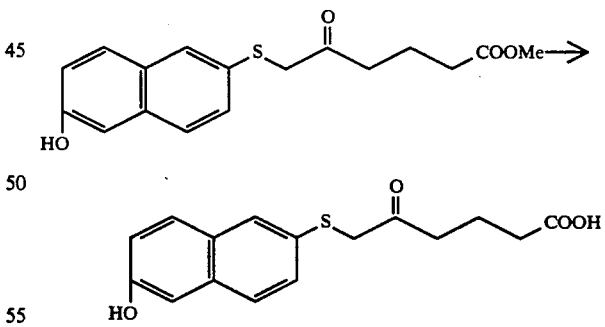

Into 48 mg (0.15 mmol) of methyl 6-(6-hydroxy-2-naphthylthio)-5-oxohexanoate were charged 1 ml of tetrahydrofuran and 2 ml of methanol, followed by stirring. An amount of 0.38 ml (0.15 mmol) of 0.4N aqueous LiOH solution was added, and the mixture stirred for one hour.

Further, 0.38 ml of 0.4N aqueous LiOH solution was added, and the mixture was stirred for two days and nights, and again 0.38 ml of 0.4N aqueous LiOH solution was added, followed by stirring for 1 hour. Saturated aqueous potassium hydrogen sulfate was added, the mixture was extracted with ether and the organic layer dried over anhydrous sulfate, and after the evaporation of the organic solvent under a reduced pressure, the desired sulfide ketone derivative was obtained by thin layer chromatography for separative recovery. Yield: 31 mg (67%).

¹H-NMR (90 MHz, CD₃OD) δ/ppm 1.86 (tt, 2H, J=6.6 Hz, 7.0 Hz), 2.15 (t, 2H, J=6.6 Hz), 2.67 (t, 2H, J=7.0 Hz), 3.34 (s, 2H), 7.03-7.71 (m, 7H), 9.61-9.80 (br, 1H).

EXAMPLE 1-15

Evaluation of activity of inhibiting lipoxygenase production in human whole blood Into 2 ml of a heparin-treated vein blood of a healthy man without administration of a drug was added 2 μl of the DMSO solution containing the test sample of the sulfide ketone derivative listed in Table 1-1 as the drug to be tested (final $10^{-5}$M). After treatment at 37° C. for 5 minutes, 10 μl of a DMSO solution of A23187 was added (final 25 μM) to carry out the treatment at 37° C. for 15 minutes, followed by ice-cooling. As the internal standard substance for quantitation, 10 μl of a DMSO solution of 100 ng of 15-HETE was added, and then 0.8 ml of acetonitrile was added and the precipitates formed were removed by centrifugation. LTB₄, 5-HETE, 12-HETE in the supernatant were separated and quantitated.

The results are shown in Table 1-1 as the lipoxygenase production inhibitory ratio.

TABLE 1-1

| Example No. | Inhibitory ratio (%) | | |
|---|---|---|---|
| (Compound) | LTB₄ | 5-HETE | 12-HETE |
| 1-4* | — | 43 | 29 |
| 1-6 | 37 | 29 | — |
| 1-11 | 64 | 56 | 28 |
| 1-12 | 2 | 6 | 17 |
| 1-14 | 37 | 49 | 20 |

*For only this compound, the results are shown in "$\times 10^{-4}$"

Example 2-1

Synthesis of methyl 6-(6-methoxy-2-naphthyl)-5-hexynoate

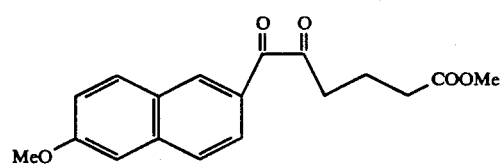

Into a solution of 2.51 g (9.2 mmol) of 6-methoxy-2-naphthyl bromide in 31 ml of diethylamine distilled with calcium hydride were charged 324 mg (0.46 mmol) of bistriphenylphosphine palladium dichloride and 192 mg of cupric iodide (1.01 mmol), followed by stirring. To the mixture was gradually added 1.06 g (9.4 mmol) of methyl 5-hexynoate, and the mixture was stirred at room temperature overnight (about 15 hours). Diethylamine was evaporated under a reduced pressure, to the residue were added ethyl acetate and water, and the mixture was extracted with ethyl acetate. Anhydrous magnesium sulfate was introduced into the organic layer for drying.

After evaporation of the solvent, the residue was subjected to silica gel column chromatography (hexane:ethyl acetate=9:1) to give 1.81 g (70%) of the desired product. ¹H-NMR (90 MHz, CDCl₃) δ/ppm (TMS) 1.88-2.10 (m, 2H), 2.45-2.72 (m, 4H), 3.69 (s, 3H), 3.60 (s, 3H), 7.07-7.81 (m, 6H, Ar)

EXAMPLE 2-2

Synthesis of methyl 6-(6-methoxy-2-naphthyl)-5,6-dioxohexanoate

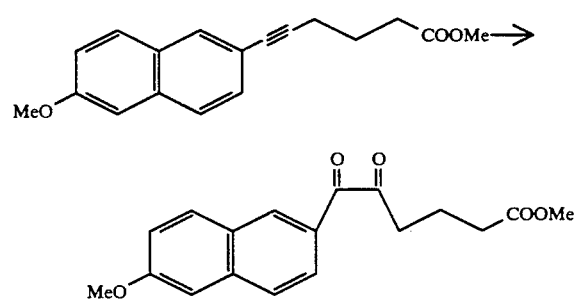

Into 1.81 g (6.4 mmol) of methyl 6(6-methoxy-2-naphthyl)hexynoate was charged 186 ml of acetone, and under stirring at room temperature, an aqueous solution of 333 mg (4.0 mmol) of sodium bicarbonate and 3.29 g (13.4 mmol) of anhydrous magnesium sulfate in 125 ml of water was added, and subsequently, 3.97 g (25.1 mmol) of potassium permanganate was added to carry out the reaction. After the reaction for 2 hours, the reaction mixture was passed through Celite-Florisil, extracted with ether, and the organic layer washed with saturated aqueous sodium chloride and dried over anhydrous magnesium sulfate. The solvent was evaporated under a reduced pressure, and the residue subjected to silica gel column chromatography (hexane:ethyl acetate=9:1→8:2) to obtain the 1,2-diketone derivative of the desired product. Yield: 1.21 g (60%).

¹H-NMR (90 MHz, CDCl₃) δ/ppm (TMS) 2.11 (tt, 2H, J=6.5 HR, 6.8 Hz), 2.47 (t, 2H, J=6.8 Hz), 3.01 (t, 2H, J=6.5 Hz), 3.69 (s, 3H), 3.96 (s, 3H), 7.12-8.46 (m, 6H)

IR (KBr tablet) 1740 (νC=O (ester)), 1730 (νC=O), 1710 (νC=O (ArCO))

(note) The product was broken when washed with saturated aqueous sodium bicarbonate.

Example 2-3

Synthesis of methyl 6-(6-methoxy-2-naphthyl)-5,6-dihydroxyiminohexanoate

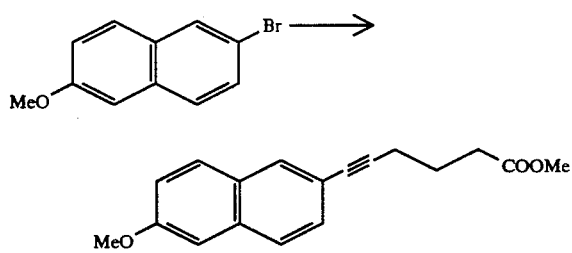

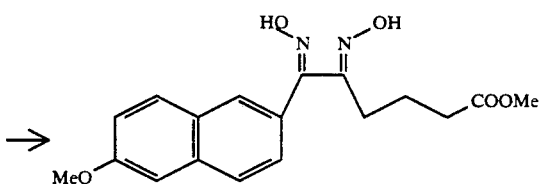

Into a reaction vessel were charged 96 mg (0.31 mmol) of methyl 6(6-methoxy-2-naphthyl)-5,6-dioxohexanoate, 85 mg (1.23 mmol) of hydroxylamine hydrochloride, suitable amounts of ethanol and water (each about 2 ml in this case) respectively, and the mixture was stirred at room temperature overnight. After extraction with ethyl acetate (for about 16 hours), the organic layer was dried by introducing anhydrous magnesium sulfate thereinto. The solvent was evaporated under a reduced pressure, and the residue subjected to silica gel column chromatography to give the 1,2-diketone derivative of the desired product. Yield: 42 mg (40%), m.p. 104.8° C.-105.5° C.

$^1$H-NMR (90 MHz, CDCl$_3$) δ/ppm 1.98 (tt, 2H, J=6.8 Hz, 6.8 Hz), 2.42 (t, 2H, J=6.8 Hz), 2.56 (t, 2H, J=6.8 Hz), 3.62 (s, 3H), 3.94 (s, 3H), 7.01-8.27 (m, 8H)

IR (KBr tablet) 3300 cm$^{-1}$ (νOH), 1740 cm$^{-1}$ (νCOOMe), 1645 cm$^{-1}$ (νC=N)

EXAMPLE 2-4

Synthesis of methyl 6-(6-hyerocy-2-naphthyl)-5,6-dioxohexanoate

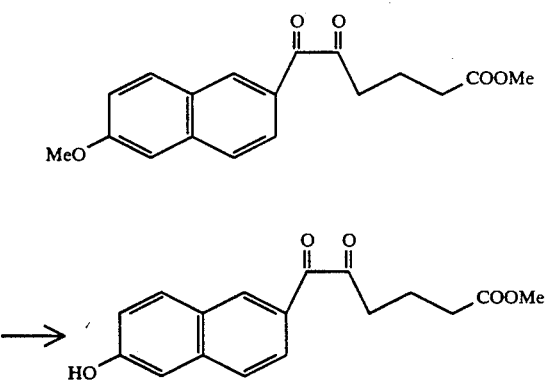

Under nitrogen atmosphere, into a reaction vessel were charged 200 mg (0.64 mmol) of methyl 6-(6-methoxy-2-naphthyl)-5,6-dioxohexanoate and 4 ml of dry methylene chloride, and the mixture was cooled to −78° C. under stirring. An amount 1.30 ml (1.30 mmol) of boron tribromide (1M methylene chloride solution) was gradually added, and the reaction was carried out at −78° C. for 3 hours and at room temperature for 25 hours. Then, after an addition of 3 ml of dry methanol, the reaction was carried out at room temperature for 3 days and nights (about 72 hours). Into the reaction mixture was charged water and ethyl acetate, and the mixture was extracted with ethyl acetate, and the organic layer was dried by introducing anhydrous magnesium sulfate thereinto. The solvent was evaporated under a reduced pressure, and the residue was subjected to silica gel column chromatography (hexane:ethyl acetate=95:5→9:1→8:2) and further to centrifugal liquid-liquid partition chromatography to give the 1,2-diketone derivative which is the desired product. 11.2 mg (6%).

$^1$H-NMR (90 MHz, CDCl$_3$) δ/ppm 2.12 (tt, 2H, J=7.0 Hz, 6.8 Hz), 2.47 (t, 2H, J=7.0 Hz), 3.01 (t, 2H, J=6.8 Hz), 3.69 (s, 3H), 5.83-5.89 (br, 1H), 7.06-8.43 (m, 6H)

IR (neat) 3400 cm$^{-1}$ (νOH), 1740 cm$^{-1}$ (νCOOMe), 1715 cm$^{-1}$, 1725 cm$^{-1}$ (νC=O)

EXAMPLE 2-5

Synthesis of methyl 6-(6-hydroxy-2-naphthyl)-5,6-dihydroxyiminohexanoate

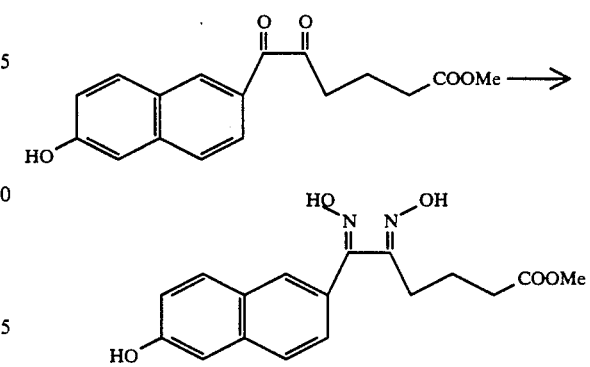

An amount of 76 mg (0.25 mmol) of methyl 6-(6-hydroxynaphthyl)-5,6-dioxohexanoate was dissolved in about 1 ml of ethanol, and 111 mg (1.6 mmol) of hydroxylamine hydrochloride was added to the solution, and suitable amounts (each about 2 ml) of ethanol and water were added to carry out the reaction at room temperature overnight. Further, 65 mg (0.93 mmol) of hydroxylamine hydrochloride was added to carry out the reaction for 2 hours. The mixture was extracted with ethyl acetate, and the organic layer was dried over anhydrous magnesium sulfate. The solvent was evaporated under a reduced pressure, and the 1,2-ketone derivative of the desired product was obtained by silica gel column chromatography (eluant: hexane:ethyl acetate=85:15→8:2→1:1). Yield: 20 mg (24%).

$^1$H-NMR (90 MHz, CDCl$_3$) δ/ppm 2.00 (m, 2H), 2.36-2.63 (m, 4H), 3.65 (s, 3H), 7.06-8.24 (m, 9H)

EXAMPLE 2-6

Synthesis of methyl 6-(6-methoxy-2-naphthyl)-6-oxohexanoate

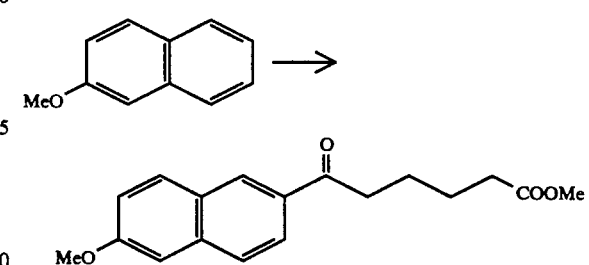

Into a solution of 6.32 g (47.4 mmol) of anhydrous aluminum chloride in 60 ml of dry nitrobenzene was added 5.03 g (31.7 mmol) of 2-methoxynaphthalene chilled with an ice bath, followed by stirring. Subsequently, under an ice bath, monomethyl adipate chloride (synthesized by adding 5.0 ml (57.3 mmol) of oxalyl chloride under an ice bath to a solution of 5.85 ml (39.5 mmol) monomethyl adipate in 50 ml of dry methylene chloride) to carry out the reaction for 6 hours, and evaporating methylene chloride and excessive oxalyl chloride under a reduced pressure) was gradually added, and the reaction was carried out at 0° C. to room temperature overnight (for 15 hours). The reaction mixture was poured into ice-water, extracted with ethyl acetate, and the organic layer was dried over anhydrous magnesium sulfate. After evaporation of the organic solvent and nitrobenzene under a reduced pressure, the desired product was obtained by silica gel chromatography. Yield: 3.82 g (40%).

$^1$H-NMR (90 MHz, CDCl$_3$) δ/ppm 1.56–1.99 (m, 4H), 2.39 (t, 2H, J=6.5 Hz), 3.09 (t, 2H, J=6.8 Hz), 3.67 (s, 3H), 3.94 (s, 3H), 7.14–8.37 (m, 6H)

EXAMPLE 2-7

Synthesis of ethyl 6-(6-methoxy-2-naphthyl)-5-hydroxvimino-6-oxohexanoate

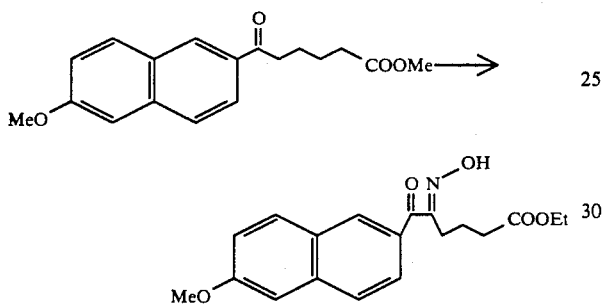

Into 2 ml ethanolic solution of 100.9 mg (0.34 mmol) of methyl 6(6-methoxy-2-naphthyl)-6-oxohexanoate were added 24.3 mg (0.35 mmol) of sodium nitrite and 245 μl (3.3 mmol) of conc. hydrochloric acid, and the mixture was stirred at room temperature. After 30 minutes, 4 ml of ethanol was again added, and stirring was continued. Then after 3 days, the mixture was extracted with ethyl acetate, and the organic layer was dried over anhydrous magnesium sulfate. The solvent was evaporated under a reduced pressure, and the desired 1,2-diketone derivative was obtained by silica gel column chromatography (eluant: hexane→hexane:ethyl acetate=8:2) and centrifugal liquid-liquid partition chromatography. Yield: 41.7 mg (36%), m.p. 94.8° C.–95.8° C.

$^1$H-NMR (90 MHz, CDCl$_3$) δ/ppm 1.23 (t, 3H, J=7.1 Hz), 1.98 (tt, 2H, J=7.0 Hz, 7.2 Hz), 2.40 (t, 2H, J=7.0 Hz), 2.81 (t, 2H, J=7.2 Hz), 3.94 (s, 3H), 4.12 (q, 2H, J=7.1 Hz), 7.12–8.42 (m, 6H, Ar), 8.42 (s, 1H)

Ir (KBr tablet) 3230 cm$^{-1}$ (νOH), 1740 cm$^{-1}$ (νC=O) 1730 cm$^{-1}$ (νC=O), 1660 cm$^{-1}$ (νC=N)

Mass (EI) m/e=343 (M+)

Example 2-8

Synthesis of methyl 6-(6-methoxy-2-naphthyl)-5-hydroxyimino-6-oxohexanoate

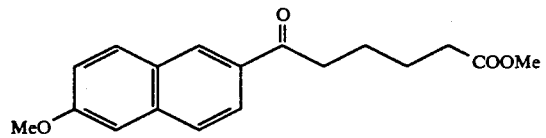

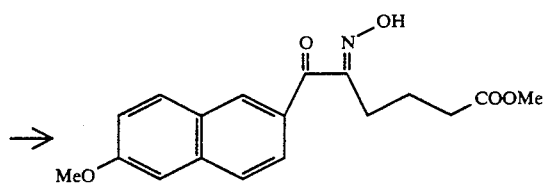

Into 6 ml methanolic solution of 203.1 mg (0.67 mmol) of methyl 6(6-methoxy-2-naphthyl)-6-oxohexanoate were added 49.7 mg (0.72 mmol) of sodium nitrite and 0.5 ml (6.7 mmol) of conc. hydrochloric acid, and the reaction was carried out at room temperature for 3 days and nights. The mixture was extracted with ethyl acetate, the organic layer dried over anhydrous magnesium sulfate, the solvent evaporated under a reduced pressure, and the desired 1,2-diketone derivative was obtained by silica gel column chromatography and centrifugal liquid-liquid partition chromatography. Yield: 38.1 mg (17%).

$^1$H-NMR (90 MHz, CDCl$_3$) δ/ppm 1.97 (tt, 2H, J=7.7 Hz, 7.7 Hz), 2.39 (t, 2H, J=7.7 Hz), 2.78 (t, 2H, J=7.7 Hz), 3.64 (s, 3H), 3.93 (s, 3H), 7.11–8.40 (m, 6H), 8.77 (brs, 1H)

IR (KBr tablet) 3250 cm$^{-1}$ (νOH), 1740 cm$^{-1}$ (νC=O) 1725 cm$^{-1}$ (νC=O), 1660 cm$^{-1}$ (νC=N)

Mass (EI) m/e=329 (M+)

Example 2-9

Synthesis of methyl 6-(6-hydroxy-2-naphthyl)-5-hydroxvimino-6-oxohexanoate

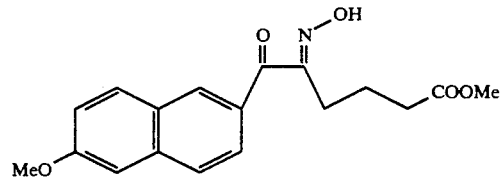

An amount 34.3 mg (0.104 mmol) of methyl 6(6-methoxy-2-naphthyl)-hydroxyimino-6-oxohexanoate was dissolved in dry methylene chloride and cooled to −78° C. Then 312 μl (0.312 mmol) of boron tribromide (1M methylene chloride solution) was added followed by stirring at −78° C. for 2 hours, and under an ice bath for 1 hour and 30 minutes. Then, to the reaction mixture was added saturated sodium bicarbonate, the mixture was extracted with ethyl acetate, and the organic layer was dried over anhydrous magnesium sulfate. The solvent was evaporated under a reduced pressure, and the 1,2-diketone derivative of the desired product was obtained by silica gel chromatography (eluant: hexane:ethyl acetate=9:1→8:2). Yield: 26.2 mg (80%).

$^1$H-NMR (90 MHz, CDCl$_3$) δ/ppm 2.00 (tt, 2H, J=6.6 Hz, 7.9 Hz), 2.44 (t, 2H, J=6.6 Hz), 2.84 (t, 2H, J=7.9 Hz), 3.67 (s, 3H), 5.30–5.36 (br, 1H), 7.09–8.41 (m, 7H)

EXAMPLE 2-10

Synthesis of methyl 6-(6-hydroxy-2-naphthyl)-5,6-dimethoximehexanoate

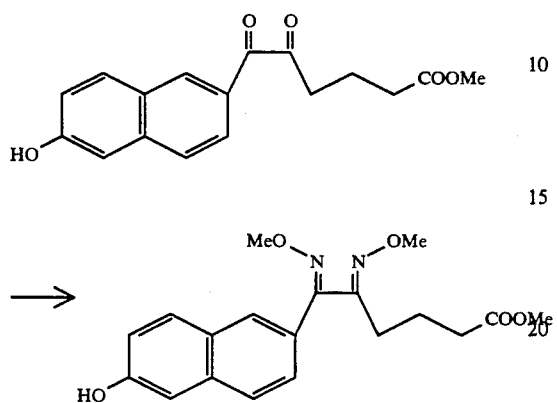

An amount of 26.9 mg (0.09 mmol) of 6-(6-hydroxy-2-naphthyl)-5,6-dioxohexanoate and 74.8 mg (0.90 mmol) of o-methylhydroxylamine hydrochloride were each dissolved in 2 ml of methanol and water, and the mixture was stirred at room temperature for 3 days. To the mixture was added 74.8 mg of o-methylhydroxylamine hydrochloride, followed by further stirring for one day. The mixture was extracted with ethyl acetate and the organic layer dried over anhydrous magnesium sulfate. The solvent was evaporated under a reduced pressure and the 1,2-diketone derivative of the desired product was obtained by silica gel column chromatography (eluant: hexane:ethyl acetate=8:2→1:1) and then centrifugal liquid-liquid partition chromatography. Yield: 5.8 mg (18%).

$^1$H-NMR (90 MHz, CDCl$_3$) [Mixture of isomers] δ/ppm 1.79–2.03 (m, 2H), 2.26–2.86 (m, 4H), 3.63 and 3.69 (s, 3H), 3.78 and 3.92 (s, 3H), 3.99 and 4.02 (s, 3H), 5.16–5.45 (br, 1H), 7.00–7.90 (m, 6H)

EXAMPLE 2-11

Evaluation of activity of inhibiting lipoxycenase production in human whole blood Into 2 ml of a heparin-treated vein blood of a healthy man without administration of a drug was added 2 μl of the DMSO solution of each compound listed in Table 2-1 (final 10$^{-4}$M). After treatment at 37° C. for 5 minutes, 10 μl of a DMSO solution of A23187 was added (final 25 μm) to carry out the treatment at 37° C. for 15 minutes, followed by ice-cooling. As the internal standard substance for quantitation, 10 μl of a DMSO solution of 100 ng of 15-HETE was added, and then 0.8 ml of acetonitrile was added and the precipitates formed were removed by centrifugation. LTB$_4$, 5-HETE, 12-HETE in the supernatant were separated and quantitated.

The results are shown in Table 2-1 as a production inhibitory ratio of LTB$_4$.

TABLE 2-1

| Example No. (Compound) | Inhibitory ratio (%) | | |
|---|---|---|---|
| | LTB$_4$ | 5-HETE | 12-HETE |
| 2-4 | 78% | 81% | 3% |
| 2-5 | 93% | 78% | 4% |

TABLE 2-1-continued

| Example No. (Compound) | Inhibitory ratio (%) | | |
|---|---|---|---|
| | LTB$_4$ | 5-HETE | 12-HETE |
| 2-9 | 66% | 77% | 27% |

EXAMPLE 3-1

Synthesis of N-hydroxy-N-(1-hydroxy-2-naphthyl)-3-methoxycarbonylpropionamide

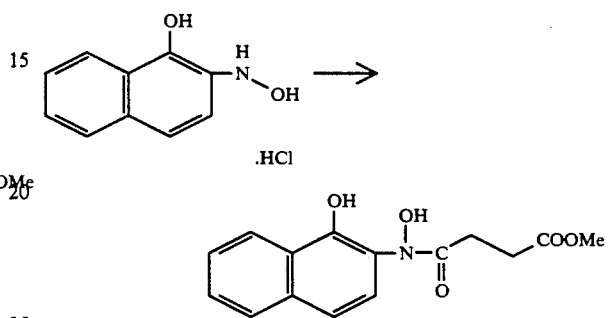

To a solution of a 1.68 g (ca. 7.9 mmol) of 1-hydroxy-2-naphthylhydroxylamine hydrochloride in THF (10 ml) and water (2 ml) was added, 1.7 ml (12 mmol) of triethylamine, followed by addition of a solution of 300 mg (2 mmol) of acid chloride of 3-methoxycarbonylpropionic acid in THF (2 ml). The mixture was stirred at room temperature for 30 minutes, the reaction was completed by an addition of aqueous KHSO$_4$, the mixture was extracted with methylene chloride, and the organic layer was dried over anhydrous magnesium sulfate.

After evaporation of the solvent under a reduced pressure, the residue was subjected to silica gel column chromatography (hexane:ethyl acetate=3:1) to give 202 mg (35%) of the hydroxyamic acid of the desired product.

NMR (δ ppm, CDCl$_3$) 2.75 (s, 4H), 3.70 (s, 3H), 6.95 (d, 1H, J=9.0 Hz), 7.2–7.8 (m, 4H), 8.1–8.5 (m, 2H), 8.35 (m, 1H)

EXAMPLE 3-2

Synthesis of N-hydroxy-N-(1-hydroxy-2-naphthyl)-4-methoxycarbonylbutanamide

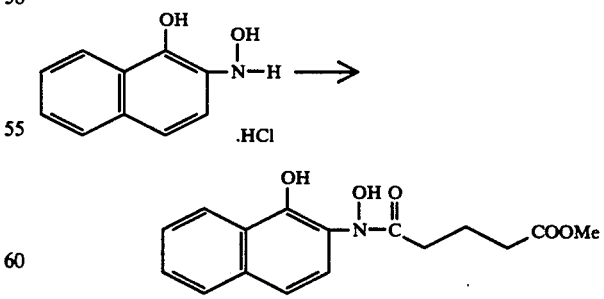

Into a solution of 2 g (9.5 mmol) of 1-hydroxy-2-naphthylhydroxylamine hydrochloride in THF (10 ml) and water (2 ml) was added 2 ml (14.2 mmol) of triethylamine, the mixture was cooled to 0° C., and 395 mg (2.4 mmol) of acid chloride of 4-methoxycarbonylbutanoic acid was added followed by stirring at room temperature. Aqueous KHSO₄ was then added and the mixture extracted with CH₂Cl₂. The organic layer was dried over anhydrous magnesium sulfate, the solvent was removed under a reduced pressure, and the residue subjected to silica gel column chromatography to give 405 mg (56%) of a hydroxyamic acid derivative.

NMR (67 ppm, CDCl₃) 1.9-2.2 (2H, m), 2.3-2.6 (m, 4H), 3.65 (3H, s), 6.95 (1H, d, J=9 Hz), 7.2-7.8 (m, 4H), 8.0 (1H, m), 8.4 (1H, m), 9.55 (1H, m)

EXAMPLE 3-3

Synthesis of N-hydroxy-N-(1-hydroxy-2-naphthyl)-4-carboxybutanamide

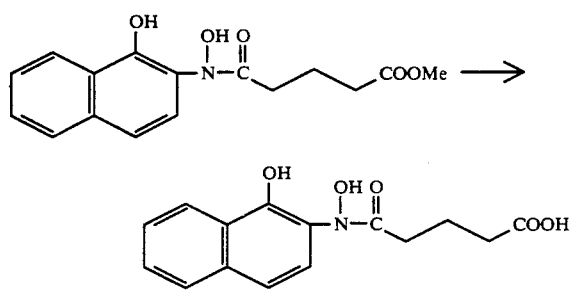

To a 4N LiOH aqueous solution of 214 mg of the methyl ester derivative in methanol (2 ml) was added THF (4 ml), and the mixture was stirred at room temperature for 14 hours. After the reaction, the mixture was extracted with an addition of water and ether, and the aqueous layer then made acidic and extracted with AcOEt. The organic layer was dried, and after a concentration of the solvent, the residue was crystallized from benzene to give the carboxylic acid derivative.

184 mg (90%)

NMR (δ ppm, CDCl₃-CD₃OD) 2-2.3 (m, 2H), 2.3-2.75 (m, 4H), 7.0-7.6 (m, 4H), 7.6-7.8 (m, 1H), 7.1-7.4 (m, 1H)

EXAMPLE 3-4

Synthesis of N-hydroxy-N-(1-hydroxy-2-naphthyl)-5-methoxycarbonylpentanamide

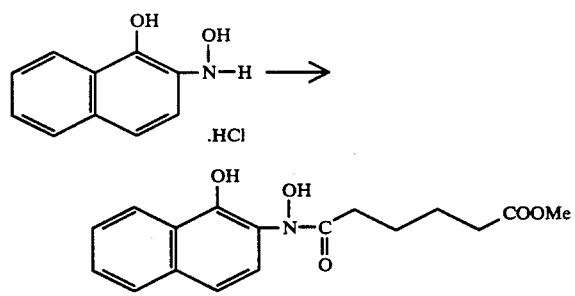

Into a 25 ml methylene chloride solution of 500 mg (3.12 mmol) of monomethyl adipate and 240 μl (3.12 mmol) of DMF was added 613 μl (7.02 mmol) of oxalyl chloride at 0° C., and the mixture was stirred as such for one hour. The mixture was then added to a solution of 3.4 g (16 mmol) of 1-hydroxy-2-naphthylhyiroxylamine hydrochloride, 3.3 ml (24 mmol) of triethylamine in THF (25 ml), and water (5 ml), at 0° C., and after stirring at 0° C. for one hour and at room temperature for one hour, the reaction was completed with aqueous KHSO₄, and the mixture was extracted with methylene chloride. The organic layer was washed with 4N HCl and then with saturated aqueous NaCl, and dried over anhydrous magnesium sulfate, and after evaporation of the solvent under a reduced pressure, the residue was subjected to silica gel column chromatography to give 762 mg (77%) of the desired product.

NMR (δ ppm, CDCl₃) 1.75 (4H, m), 2.35 (4H,m), 3.70 (3H, s), 6.95 (d, 1H, J=9 Hz), 7.2-7.55 (m, 3H), 7.7 (1H, m), 8.05 (1H, m), 8.45 (1H, m), 9.70 (1H, S Like)

Recrystallization (benzene) mp. 111°-113° C.

EXAMPLE 3-5

Synthesis of N-hydroxy-N-(1-hydroxy-2-naphthyl)-6-methoxycarbonylhexanamide

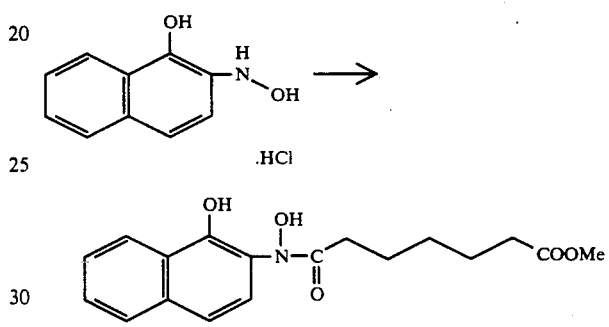

Into a 25 ml methylene chloride solution of 500 mg (2.87 mmol) of 6-methoxycarbonylhexanoic acid and 222 μl (2.87 mmol) of DMF was added 564 μl (6.46 mmol) of oxalyl chloride at 0° C., and the mixture was stirred as such for one hour. The mixture was then added to a solution of 3.17 g (15 mmol) of 1-hydroxy-2-naphthylhydroxylamine ˙ hydrochloride, 3.1 ml (23 mmol) of triethylamine in THF (25 ml), and water (5 ml), at 0° C., and after stirring at 0° C. for one hour and at room temperature for one hour, the reaction was completed with aqueous KHSO₄, and the mixture was extracted with methylene chloride. The organic layer was washed with 4N HCl and with saturated aqueous NaCl, and then dried over anhydrous magnesium sulfate, and after evaporation of the solvent under a reduced pressure, the residue was subjected to silica gel column chromatography to give 738 mg (78%) of the desired product.

NMR (δ ppm, CDCl₃)

1.2-2.0 (m, 6H), 2.25-2.6 (m, 4H), 3.7 (s, 3H), 7.05 (d, 1H, J=9 Hz), 7.2-8.0 (m, 5H), 8.4 (m, 1H), 9.7 (m, 1H)

EXAMPLE 3-6

Synthesis of N-hydroxy-N-(1-hydroxy-2-naphthyl)-4-methoxycarbonyl-3-oxabutanamide

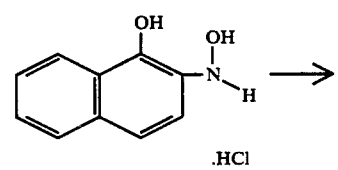

-continued

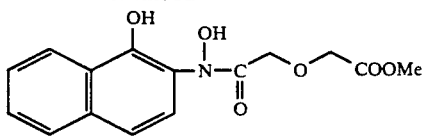

Into a 25 ml methylene chloride solution of 500 mg (3.38 mmol) of methyl diglycolate and 200 μl (3.38 mmol) of DMF was added 660 μl (7.60 mmol) of oxalyl chloride at 0° C., and the mixture was stirred as such for one hour. The mixture was added to a solution of 3.6 g (17 mmol) of 1-hydroxy-2-naphthylhydroxylamine hydrochloride, 3.5 ml (25 mmol) of triethylamine in THF (25 ml), and water (5 ml), at 0° C., and after stirring at 0° C. for one hour and at room temperature for one hour, the reaction was completed with aqueous $KHSO_4$, and the mixture was extracted with methylene chloride. The organic layer was washed with 4N HCl and with saturated aqueous NaCl, and then dried over anhydrous magnesium sulfate, and after evaporation of the solvent under a reduced pressure, the residue was subjected to silica gel column chromatography to give 710 mg (69%) of the desired product.

NMR (δ ppm, $CDCl_3$) 3.70 (s, 3H), 4.29 (s, 2H), 4.30 (s, 2H), 7.15–7.90 (m, 5H), 8.4–8.6 (m, 1H), 9.35 (m, 1H), 9.85 (m, 1H)

EXAMPLE 3-7

Synthesis of N-hydroxy-N-(2-naphthylmethyl)-3-methoxycarbonyl-propionamide

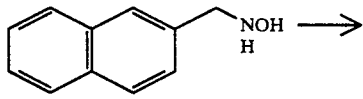

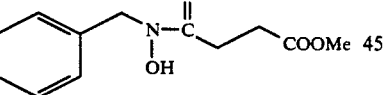

Into a solution of 52 mg (0.3 mmol) of 2-naphthylmethylhydroxylamine in THF (5 ml) and water (1 ml) was added 30 mg (0.3 mmol) of triethylamine, and then a solution of 40 mg (0.3 mmol) of acid chloride of 3-methoxycarbonylpropionic acid in THF (1 ml), followed by stirring at room temperature for330 minutes. 1N-HCl (5 ml) was then added, and the desired product was extracted with methylene chloride. The extract was successively washed with water, aqueous NaCl, and then dried over anhydrous magnesium sulfate to give 82 mg (95%) of a crude product, which was recrystallized from methylene chloride and n-hexane to obtain 50 mg (58%) of colorless crystals.

m.p. 91.5°–92° C.

1H-NMR (δ ppm, $CDCl_3$): 2.73 (s, 4H), 3.63 (s, 3H), 4.95 (s, 2H), 7.3–8.0 (m, 8H)

IR ($cm^{-1}$, KBr): 3180, 2940, 1730, 1605, 1230, 1170, 830, 750

EXAMPLE 1-8

Synthesis of N-hydroxy-N-(2-naphthylmethyl)-4methoxycarbonyl-butanamide

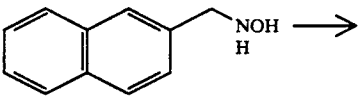

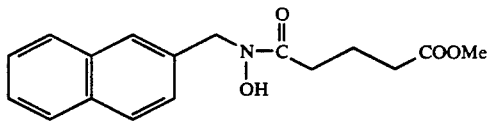

Into a solution of 52 mg (0.3 mmol) of 2-naphthylmethylhydroxylamine in THF (5 ml) and water (1 ml) was added 30 mg (0.3 mmol) of triethylamine, and then a solution of 49 mg (0.3 mmol) of acid chloride of 4-methoxycarbonylbutanoic acid in THF (1 ml), followed by stirring at room temperature for 30 minutes. 1N-HCl (5 ml) was added and the desired product was extracted with methylene chloride. The extract was successively washed with water, aqueous NaCl, and then dried over anhydrous magnesium sulfate to give a purified product, which was then subjected to silica gel column chromatography to obtain 58 mg (64%) of the desired product.

NMR (δ ppm, $CDCl_3$): 1.98 (q, 2H, J=6.0 Hz), 2.2–2.6 (m, 4H), 3.60 (s, 3H), 4.93 (s, 2H), 7.3–8.0 (m, 8H)

IR ($cm^{-1}$, KBr): 3150, 2900, 1730, 1600, 1460, 1340, 1270

Recrystallization (methylene chloride-n-hexane) m.p. 109°–110° C.

EXAMPLE 3-9

Synthesis of N-hydroxy-N-(1-methoxy-2-naphthylmethyl)-4-methoxycarbonylbutanamide

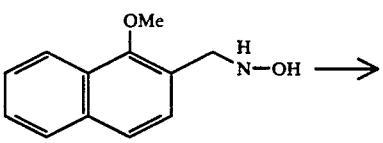

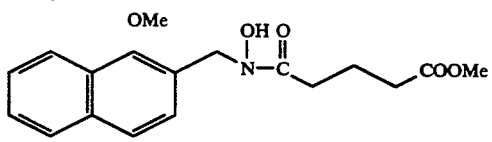

Into a solution of 267 mg (1.33 mmol) of 1-methoxy-2-naphthylmethylhydroxylamine and 185 μl (1.33 mmol) of triethylamine in THF (15 ml) and water (3 ml) was added under 0° C. a solution of 219 mg (1.33 mmol) of acid chloride of 4-methoxycarbonylbutanoic acid in THF (3 ml), followed by stirring at 0° C. for one hour and at room temperature for one hour. After the reaction, an aqueous potassium hydrogen sulfate was added, and the mixture extracted with methylene chloride. The organic layer was dried over anhydrous magnesium sulfate, and the solvent was evaporated under a reduced pressure. The crude product obtained was subjected to silica gel column chromatography (hexane: ethyl acetate=1:1) to give 279 mg (64%) of the desired product.

NMR (δ ppm, CDCl₃): 1.8-2.1 (m, 2H), 2.2-2.7 (m, 4H), 3.60 (s, 3H), 3.95 (s, 3H), 5.0 (s, 2H), 7.25-8.15 (m, 6H)

EXAMPLE 3-10

Synthesis of N-hydroxy-N-(1-hydroxy-2-naphthyl)-3-methoxycarbonylbenzamide

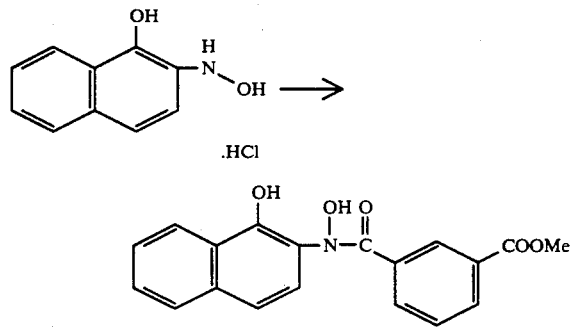

Into a 25 ml dry methylene chloride solution of 500 mg (2.78 mmol) of monomethyl isophthalate and 215 μl (2.78 mmol) of DMF was added under N₂ atmosphere 546 μl (6.26 mmol) of oxalyl chloride at 0° C., and subsequently, the mixture was returned to room temperature and stirred for one hour. The mixture was added dropwise under an N₂ atmosphere to a solution of 1.76 g (8.34 mmol) of 1-hydroxy-2-naphthylhydroxylamine hydrochloride, 2.9 ml (21 mmol) of triethylamine in THF (25 ml), and water (5 ml), followed by stirring as such at room temperature for one hour. The reaction was completed by an addition of 4N hydrochloric acid, and the mixture extracted with methylene chloride. The organic layer was washed with 4N hydrochloric acid, water, and saturated aqueous sodium chloride, and dried over anhydrous magnesium sulfate. The solvent was evaporated under a reduced pressure, and the crude product obtained was subjected to silica gel column chromatography (hexane:ethyl acetate 6:1→4:1) to give 513 mg (55%) hydroxyamic acid.

NMR (δ ppm, CDCl₃): 3.97 (s, 3H), 7.1-7.8 (m, 6H), 8.1-8.6 (m, 5H), 9.4 (br, s, 1H)

EXAMPLE 3-11

Synthesis of N-hydroxy-N-(1-hydroxy-2-naphthyl)-2-methoxycarbonylmethylbenzamide

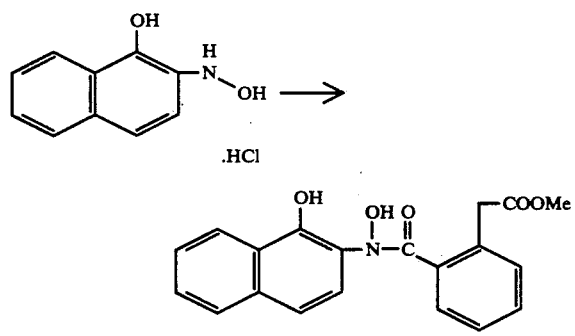

Into a 30 ml dry methylene chloride solution of 830 mg (4.27 mmol) of monomethyl homophthalate and 330 μl (4.27 mmol) of DMF was added under an N₂ atmosphere 840 μl (9.6 mmol) of oxalyl chloride at 0° C., and subsequently, the mixture was returned to room temperature and stirred for one hour. The mixture was added dropwise under an N₂ atmosphere to a solution of 1.80 g (8.53 mmol) of 1-hydroxy-2-naphthylhydroxylamine hydrochloride, 4.24 ml (30.5 mmol) of triethylamine in THF (30 ml), and water (6 ml), followed by stirring as such at room temperature for one hour. The reaction was completed by an addition of 4N hydrochloric acid, and the mixture extracted with methylene chloride. The organic layer was washed with 4N hydrochloric acid, water, and saturated aqueous sodium chloride, and dried over anhydrous magnesium sulfate. The solvent was evaporated under a reduced pressure, and the crude product obtained was subjected to silica gel column chromatography (hexane:ethyl acetate 6:1→4:1) to give 776 mg (52%) of hydroxamic acid.

NMR (δ ppm, CDCl₃): 3.70 (s, 3H), 3.90 (s, 2H), 7.0-7.8 (m, 9H), 8.3-8.45 (m, 1H), 9.3 (br, s, 1H), 9.55 (br, s, 1H)

EXAMPLE 3-12

Evaluation of activity of inhibiting lipoxygenase production in human whole blood Into 1 ml of a heparin-treated vein blood of a healthy man without administration of a drug was added 1 μl of the DMSO solution of each compound listed in Table 3-1 (final $10^{-5}$M). After treatment at 37° C. for 5 minutes, 5 μl of a DMSO solution of calcium ionophone (A23187, 25 μM) was added to carry out the treatment at 37° C. for 15 minutes, followed by ice-cooling. As the internal standard substance for quantitation, 10 μl of a DMSO solution of 100 ng of 15-HETE was added, then 0.8 ml of acetonitrile was added, and the precipitates formed were removed by centrifugation. LTB₄, 5-HETE in the supernatant were separated and quantitated, and the results are shown as the production inhibitory ratio of LTB₄, etc. in Table 3-1.

TABLE 3-1

| Example No. (Compound) | Inhibitory ratio (%) | |
|---|---|---|
| | LTB₄ | 5-HETE |
| 3-2 | — | 80% |
| 3-4 | 45% | 38% |
| 3-5 | 39% | 40% |
| 3-6 | 24% | 18% |
| 3-7 | 71% | 59% |
| 3-8 | 60% | 59% |
| 3-9 | 40% | 27% |
| 3-10 | 63% | 45% |

EXAMPLE 3-13

Evaluation of activity of inhibiting lipoxygenase production is not basophilic leuchemia (RBL-1) cells A 5×10⁶ amount cells of RBL-1 were used and the DMSO solution of each compound listed in Table 3-2 was added thereto so that the final concentration was obtained. After incubation at 37° C. for 5 minutes, 50 μg of arachidonic acid and 25 μM of calcium ionophole (A23187) were added thereto, followed by incubating at 37° C. for 15 minutes. The extraction was carried out after the reaction was completed. The product was determined by reversed phase HPLC.

The results are shown in Table 3-2.

TABLE 3-2

| Example No. (Compound) | $L_{onc}$ | Inhibitory ratio (%) $LTB_4$ |
|---|---|---|
| 3-3 | $10^{-6}M$ | 35% |
|  | $10^{-7}M$ | 20% |
| 1-12 | $10^{-6}M$ | 53% |
|  | $10^{-7}M$ | 27% |
|  | $10^{-8}M$ | 28% |

We claim:

1. A naphthalene derivative of formula (I):

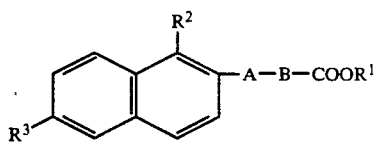

wherein $R^1$ represents a hydrogen atom, a $C_1$-$C_5$ alkyl group or a non-toxic salt moiety;

$R^2$ and $R^3$ independently represents a hydrogen atom or —$OR^4$ where $R^4$ represents a hydrogen atom or a $C_1$-$C_3$ alkyl group;

A represents a group:

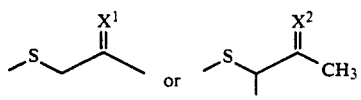

where $X^1$ and $X^2$ represents an oxygen atom or N—$OR^5$, where $R^5$ represents a hydrogen atom or a $C_1$-$C_3$ alkyl group, a group:

where $Y^1$ and $Y^2$ independently represent an oxygen atom or a group N—$OR^6$, where $R^6$ represents a hydrogen atom or a $C_1$-$C_3$ alkyl group, or a group:

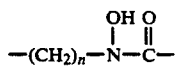

where n is 0 or 1; and
B represents —$(CH_2)_m$—
wherein m is an integer of 1 to 8,

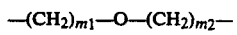

where $m_1$ and $m_2$ are independently 1 or 2, or

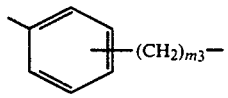

wherein $m_3$ is 0 or 1.

2. A naphthalene derivative as claimed in claim 1, wherein, when $R^2$ is a hydrogen atom and $R^3$ is a hydrogen atom, a hydroxyl group, or a methoxy group;
A is a group:

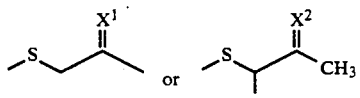

where $X^1$ and $X^2$ are an oxygen atom or a group N—$OR^5$, where $R^5$ is a hydrogen atom or a methyl group or a group:

where $Y^1$ and $Y^2$ are independently an oxygen atom or a group N—$OR^6$, where $R^6$ is a hydrogen atom or a methyl group.

3. A naphthalene derivative as claimed in claim 2, wherein B is —$(CH_2)_m$—, where m is an integer of 1 to 4.

4. A naphthalene derivative as claimed in claim 1, wherein, when $R^2$ is a hydrogen atom, a hydroxyl group, or a methoxy group and when $R^3$ is a hydrogen atom, A is a group:

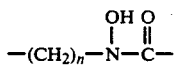

where n is 0 or 1.

5. A naphthalene derivative as claimed in claim 4, wherein B is a group:

where m is 2 to 5.

6. A naphthalene derivative as claimed in claim 4, wherein B is a metaphenylene group:

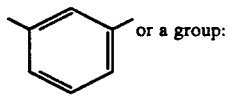

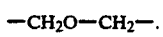

7. A naphthalene derivative as claimed in claim 1, wherein $R^1$ is a hydrogen atom or a methyl group.

* * * * *